United States Patent
Yoshida et al.

(10) Patent No.: US 9,255,114 B2
(45) Date of Patent: Feb. 9, 2016

(54) METHOD FOR PRODUCING FLUORINE-CONTAINING SUBSTITUTED COMPOUND AND FLUORINE-CONTAINING SUBSTITUTED COMPOUND

(71) Applicants: Kyoto University, Kyoto (JP); Taiyo Nippon Sanso Corporation, Tokyo (JP)

(72) Inventors: Junichi Yoshida, Kyoto (JP); Aiichiro Nagaki, Kyoto (JP)

(73) Assignees: KYOTO UNIVERSITY, Kyoto (JP); TAIYO NIPPON SANSO CORPORATION, Tokyo (JP)

(*) Notice: Subject to any disclaimer, the term of this patent is extended or adjusted under 35 U.S.C. 154(b) by 127 days.

(21) Appl. No.: 14/021,049

(22) Filed: Sep. 9, 2013

(65) Prior Publication Data

US 2014/0012027 A1 Jan. 9, 2014

Related U.S. Application Data

(63) Continuation of application No. PCT/JP2012/055868, filed on Mar. 7, 2012.

(30) Foreign Application Priority Data

Mar. 10, 2011 (JP) ................. 2011-053290

(51) Int. Cl.
*C07F 7/00* (2006.01)
*C07F 7/04* (2006.01)
(Continued)

(52) U.S. Cl.
CPC . *C07F 9/28* (2013.01); *C07C 29/40* (2013.01); *C07C 29/62* (2013.01); *C07C 33/20* (2013.01);
(Continued)

(58) Field of Classification Search
CPC .......... C07F 7/12; C07F 7/122; C07F 7/2212; C07F 9/28; C07C 29/62; C07C 33/20; C07C 45/00; C07C 49/80; C07C 231/00; C07C 233/13; C07C 233/15
USPC .................. 556/95, 476, 488; 564/209, 214; 568/16, 308, 316, 812
See application file for complete search history.

(56) References Cited

U.S. PATENT DOCUMENTS

2008/0194816 A1 8/2008 Yoshida et al.
2012/0129077 A1 5/2012 Hirakimoto et al.

FOREIGN PATENT DOCUMENTS

DE 239788 10/1986
JP 58-065233 4/1983
(Continued)

OTHER PUBLICATIONS

Gassman, P.G., et al., "Nucleophilic Addition of the Pentafluoroethyl Group to Aldehydes, Ketones, and Esters," J. Org. Chem., vol. 52, 1987, pp. 2481-2490.
(Continued)

*Primary Examiner* — Porfirio Nazario Gonzalez
(74) *Attorney, Agent, or Firm* — Carmody Torrance Sandak & Hennessey LLP

(57) ABSTRACT

A method for producing a fluorine-containing substituted compound, the method including: introducing an organofluorine compound and an organolithium compound into a microreactor provided with a flow path capable of mixing a plurality of liquids, to thereby obtain a reaction product; and introducing, into the microreactor, the reaction product and an electrophile exhibiting electrophilic effect on the reaction product, to thereby obtain a fluorine-containing substituted compound.

19 Claims, 6 Drawing Sheets

(51) Int. Cl.
| | |
|---|---|
| C07F 9/28 | (2006.01) |
| C07C 231/10 | (2006.01) |
| C07F 9/50 | (2006.01) |
| C07C 29/40 | (2006.01) |
| C07C 45/45 | (2006.01) |
| C07F 7/08 | (2006.01) |
| C07F 7/22 | (2006.01) |
| C07C 29/62 | (2006.01) |
| C07C 33/20 | (2006.01) |
| C07C 45/00 | (2006.01) |
| C07C 49/80 | (2006.01) |
| C07C 231/00 | (2006.01) |
| C07C 233/13 | (2006.01) |
| C07C 233/15 | (2006.01) |
| C07F 7/12 | (2006.01) |
| C07C 33/46 | (2006.01) |
| C07C 33/48 | (2006.01) |

(52) U.S. Cl.
CPC .............. *C07C 33/46* (2013.01); *C07C 33/483* (2013.01); *C07C 45/00* (2013.01); *C07C 45/455* (2013.01); *C07C 49/80* (2013.01); *C07C 231/00* (2013.01); *C07C 231/10* (2013.01); *C07C 233/13* (2013.01); *C07C 233/15* (2013.01); *C07F 7/0809* (2013.01); *C07F 7/12* (2013.01); *C07F 7/122* (2013.01); *C07F 7/2212* (2013.01); *C07F 9/5022* (2013.01); *C07F 9/5068* (2013.01)

(56) References Cited

FOREIGN PATENT DOCUMENTS

| JP | 61-148203 | 7/1986 |
| JP | 2004-267966 | 9/2004 |
| JP | 2005-091812 | 4/2005 |
| JP | 2006-241065 | 9/2006 |
| JP | 2008-007415 | 1/2008 |
| JP | 2008-195639 | 8/2008 |
| JP | 2010-033732 | 2/2010 |
| JP | 2010-077351 | 4/2010 |
| JP | 2010-120935 | 6/2010 |
| JP | 2010-248138 | 11/2010 |
| JP | 2011-034829 | 2/2011 |

OTHER PUBLICATIONS

Shimizu, M., et al., "Generation and Carbonyl Addition Reactions of Dibromofluoromethyllithium Derived from Tribromofluoromethane as Applied to the Stereoselective Synthesis of Fluoro Olefins and 2-Bromo-2-fluoro-1,3-alkanediols," Bull. Chem. Soc. Jpn., vol. 71, No. 12, 1998, pp. 2903-2921.

Nadano, R., et al., "Rapid and Slow Generation of 1-Trifluoromethylvinyllithium: Syntheses and Applications of $CF_3$-Containing Allylic Alcohols, Allylic Amines, and Vinyl Ketones," Chemistry—An Asian Journal, vol. 5, 2010, pp. 1875-1883.

Chen, Q., et al., "Stereoselective Construction of the 1,1,1-trifluoroisopropyl moiety by asymmetric hydrogenation of 2-(trifluoromethyl)allylic alcohols and its Application to the Synthesis of a trifluoromethylated amino diol," Tetrahedron, vol. 63, 2007, pp. 11965-11972.

Clackers, M., et al., "Non-Steroidal Glucocorticoid Agonists—The Discovery of Aryl Pyrazoles as A-ring Mimetics," Bioorganic & Medicinal Chemistry Letters, vol. 17, 2007, pp. 4737-4745.

METHOD FOR PRODUCING FLUORINE-CONTAINING SUBSTITUTED COMPOUND AND FLUORINE-CONTAINING SUBSTITUTED COMPOUND

CROSS-REFERENCE TO RELATED APPLICATION

This application is a continuation application of International Application PCT/JP2012/055868, filed on Mar. 7, 2012 and designated the U.S., the entire contents of which are incorporated herein by reference.

BACKGROUND OF THE INVENTION

1. Field of the Invention

The present invention relates to a method for producing a fluorine-containing substituted compound by using a microreactor and a novel fluorine-containing substituted compound.

2. Description of the Related Art

The introduction of a fluorine atom and a fluorine-containing substituent into a molecule occupies a position essential for drug design in the fields of, for example, medicines and agricultural chemicals, because of the specific properties possessed by fluorine; examples have been reported in which the introduction of fluorine atoms into biologically active substances including biologically active peptides gives rise to, for example, the increase of the activity, the increase of the stability and the increase of the lipophilicity in the biologically active substances (see, for example, Takeo Taguchi, Synthesis and Application of Fluorine-Based Biologically Active Substances, 2005, CMC Publishing Co. Ltd.).

This is due to the mimic effect such that even a biologically active substance including carbon-hydrogen bonds partially replaced with carbon-fluorine bonds is incorporated into the metabolic system in a sterically almost indistinguishable manner because of the smallness of the size of the fluorine atom, and also due to the blocking effect such that such a biologically active substance generally hardly undergoes the metabolism in the body because of the extreme stability of the carbon-fluorine bond.

The fluorine atom has unique properties different from the properties of other atoms, typified by remarkable water repellency, oil repellency and heat resistance; accordingly, fluorine is expected to help the development of functional materials, and successful examples of such development include liquid crystal materials, and application of such functional materials to the electrolyte membranes of fuel cells (for example, see Japanese Patent Application Laid-Open (JP-A) Nos. 2010-248138, 2010-077351 and 2011-034829).

Such introduction of fluorine atoms or fluorine-containing substituents into molecules offers one of the most effective methods in designing, for example, medicines and agricultural chemicals, and in developing functional materials; thus the development of efficient synthesis methods of fluorine-containing substituted compounds has come to be regarded as important.

Currently most frequently found synthesis methods of fluorine-containing organic compounds are those methods which use as starting materials fluorine-containing compound relatively inexpensive and available in large amounts, and synthesize the target compounds by taking advantage of common organic synthesis reactions. Among such methods, those methods which take advantage of radical reactions are most common because radical reactions can form extremely simply organofluorine compound active species (radicals) from precursors such as organofluorine compounds.

There have hitherto been known methods using organofluorine compounds and organolithium compounds, and producing fluorine-containing substituted compounds on the basis of the reactions by way of fluorine-substituted lithium carbenoid species as the foregoing active species.

For example, a method is reported in which pentafluoroethyl iodide, benzaldehyde and methyllithium are added in a batch-type reactor and are allowed to react with each other (see J. Org. Chem., 1987, Vol. 52, p. 2482). In this method, the halogen-lithium exchange reaction between pentafluoroethyl iodide and methyllithium forms pentafluoroethyllithium, as a highly reactive fluorine-substituted carbenoid species, and a substitution reaction occurring between pentafluoroethyllithium and benzaldehyde as an electrophile produces the target fluorine-containing substituted compound.

Another method is also reported in which tribromofluoromethane, naphthylaldehyde and n-butyllithium are added in a batch-type reactor and are allowed to react with each other (see Bull. Chem. Soc. J., 1998, Vol. 71, p. 2903). In this method, the halogen-lithium exchange reaction between tribromofluoromethane and n-butyllithium forms dibromofluoromethyllithium, as a fluorine-substituted carbenoid species, and a substitution reaction occurring between dibromofluoromethyllithium and naphthylaldehyde as an electrophile produces the target fluorine-containing substituted compound.

The fluorine-substituted lithium carbenoid species is one of the active species highest in reactivity, but is on the other hand extremely unstable and tends to form a fluoroalkene through β-elimination. Accordingly, for the purpose of taking advantage of the unstable fluoroalkyllithium for the synthesis reaction of the fluorine-containing substituted compound, an excessive amount of fluoroalkyl halide is required, and it is required to perform the reaction under a low temperature condition of −78° C. and by allowing beforehand an electrophile exhibiting electrophilic effect to be concomitantly present in the batch-type reactor. Further, some of the fluorine-substituted lithiumcarbenoid species are unstable under a low temperature condition of −100° C., and cannot be used for the synthesis reaction of the fluorine-containing substituted compounds. Consequently, the industrial realization of the foregoing method involves extreme difficulty.

The generation of the active species (radical) depends on the strength of the reactivity between the organolithium compound and the organofluorine compound and the strength of the reactivity between the organolithium compound and the electrophile, and hence there is a problem such that such an electrophile that is higher in reactivity than the organofluorine compound used cannot be used.

Thus, according to the present state of affairs, the following methods for producing a fluorine-containing substituted compound have been awaited: a method for producing a fluorine-containing substituted compound, capable of producing a fluorine-containing substituted compound under industrially practicable temperature conditions, by using a simple apparatus and simple operations; and a method for producing a fluorine-containing substituted compound, capable of widening the range of selection of the electrophile and thus producing novel fluorine-containing substituted compounds.

SUMMARY OF THE INVENTION

An object of the present invention is to provide a method for producing a fluorine-containing substituted compound, capable of producing a fluorine-containing substituted compound under industrially practicable temperature conditions, by using a simple apparatus and simple operations. Another object of the present invention is to provide a method for producing a fluorine-containing substituted compound, capable of improving the yield of the fluorine-containing substituted compound that is low in yield when produced with a conventional production method, and capable of producing a novel fluorine-containing substituted compound that cannot be produced with a conventional production method. Yet another object of the present invention is to provide a novel fluorine-containing substituted compound.

In order to solve the foregoing technical problem, the present inventors made a diligent study and consequently have obtained the following findings. Specifically the present inventors have obtained the findings such that by using a microreactor having a simple structure and by taking advantage of the features of the microreactor such as high speed mixing, detailed temperature control and precise residence time control, an efficient method for producing a fluorine-containing substituted compound can be realized, and a novel fluorine-containing substituted compound can be produced.

The present invention is based on the foregoing findings obtained by the present inventors, and the solution for the technical problem is specifically as follows.

<1> A method for producing a fluorine-containing substituted compound, the method including:
introducing an organofluorine compound and an organolithium compound into a microreactor provided with a flow path capable of mixing a plurality of liquids, to thereby obtain a reaction product; and
introducing, into the microreactor, the reaction product and an electrophile exhibiting electrophilic effect on the reaction product, to thereby obtain a fluorine-containing substituted compound.

<2> The method according to <1>, wherein the organofluorine compound is a fluoroalkyl halide having 6 carbon atoms, and a temperature T (° C.) inside the microreactor into which the organofluorine compound and the organolithium compound have been introduced and the residence time t (sec) in the microreactor satisfy the following relation:

$T \le -3.8t - 48$

<3> The method according to <1>, wherein the organofluorine compound is a fluoroalkyl halide having 2 carbon atoms, and a temperature T (° C.) inside the microreactor into which the organofluorine compound and the organolithium compound have been introduced and the residence time t (sec) in the microreactor satisfy the relations $-100 \le T \le 0$ and $0.15 \le t \le 8.4$, respectively.

<4> The method according to <1>, wherein the organofluorine compound is a fluoroalkyl halide having 3 carbon atoms, and a temperature T (° C.) inside the microreactor into which the organofluorine compound and the organolithium compound have been introduced and a residence time t (sec) thereof in the microreactor satisfy the following relation:

$T \le -3.2t - 45$.

<5> The method according to <1>, wherein the organofluorine compound is a fluoroalkyl halide having 4 carbon atoms, and a temperature T (° C.) inside the microreactor into which the organofluorine compound and the organolithium compound have been introduced and a residence time t (sec) thereof in the microreactor satisfy the following relation:

$T \le -5.1t - 47$.

<6> The method according to <1>, wherein the organofluorine compound is a fluoroalkyl halide having 5 carbon atoms, and a temperature T (° C.) inside the microreactor into which the organofluorine compound and the organolithium compound have been introduced and a residence time t (sec) thereof in the microreactor satisfy the following relation:

$T \le -7.1t - 47$.

<7> The method according to any one of <1> to <6>, further including: continuously introducing, into the microreactor, the fluorine-containing substituted compound and methanol.

<8> The method according to any one of <1> to <7>, wherein the organofluorine compound, the organolithium compound and the electrophile are dissolved in diethyl ether and introduced into the microreactor.

<9> The method according to any one of <1> to <8>, wherein the organofluorine compound is a perfluoroalkyl halide.

<10> The method according to any one of <1> to <9>, wherein the organolithium compound is butyllithium.

<11> The method according to any one of <1> to <10>, wherein the electrophile is an aldehyde, a ketone or an isocyanate, or any combination thereof.

<12> A method for producing a fluorine-containing substituted compound, the method including:
introducing, into a microreactor provided with a flow path capable of mixing a plurality of liquids, an organofluorine compound, an organolithium compound, and an electrophile exhibiting electrophilic effect on the reaction product between the organofluorine compound and the organolithium compound, under conditions of temperature being −55° C. or higher.

<13> The method according to <12>, wherein the temperature is −20° C. or higher.

<14> The method according to <12> or <13>, wherein the temperature is 0° C. or higher.

<15> The method according to any one of the foregoing <12> to <14>, further including continuously introducing, into the microreactor, the fluorine-containing substituted compound and methanol.

<16> The method according to any one of <12> to <15>, wherein the organofluorine compound, the organolithium compound and the electrophile are dissolved in diethyl ether and introduced into the microreactor.

<17> The method according to any one of <12> to <16>, wherein the organofluorine compound is a perfluoroalkyl halide.

<18> The method according to any one of <12> to <17>, wherein the organolithium compound is butyllithium.

<19> The method according to any one of <12> to <18>, wherein the electrophile is an aldehyde, a ketone or an isocyanate, or any combination thereof.

<20> A fluorine-containing substituted compound represented by any one of the following general formulas (1) to (10):

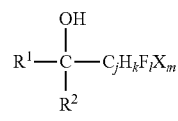

General Formula (1)

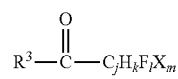

General Formula (2)

-continued

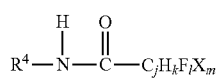

General Formula (3)

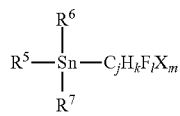

General Formula (4)

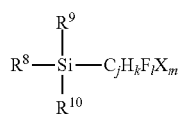

General Formula (5)

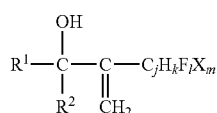

General Formula (6)

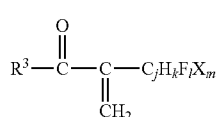

General Formula (7)

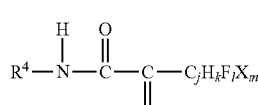

General Formula (8)

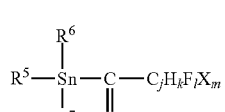

General Formula (9)

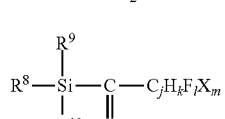

General Formula (10)

where, in the general formulas (1) to (10), $R^1$ and $R^3$ to $R^{10}$ may be the same as or different from each other, each represent an aliphatic group having 1 to 9 carbon atoms which may have a substituent, an aromatic group having 3 to 19 carbon atoms which may have a substituent, or a heterocyclic group having 3 to 19 carbon atoms which may have a substituent; $R^2$ represents a hydrogen atom, an aliphatic group having 1 to 9 carbon atoms which may have a substituent, an aromatic group having 3 to 19 carbon atoms which may have a substituent, or a heterocyclic group having 3 to 19 carbon atoms which may have a substituent; X represents a halogen atom other than a fluorine atom; and j, k, l and m satisfy the relation $2j+1=k+l+m$, where j is an integer of 1 to 20, k and m are each an integer of 0 or more, and l is an integer of 1 or more.

The present invention can solve the foregoing conventional problems and can achieve the foregoing objects, and can provide a method for producing a fluorine-containing substituted compound capable of producing a fluorine-containing substituted compound under industrially practicable temperature conditions, by using a simple apparatus and simple operations. The present invention can improve the yield of the fluorine-containing substituted compound that is low in yield when produced with a conventional production method. The present invention can also provide a method for producing a fluorine-containing substituted compound, capable of producing a novel fluorine-containing substituted compound that cannot be produced with a conventional production method. Herewith, the present invention can provide a novel fluorine-containing substituted compound.

Figure 1:
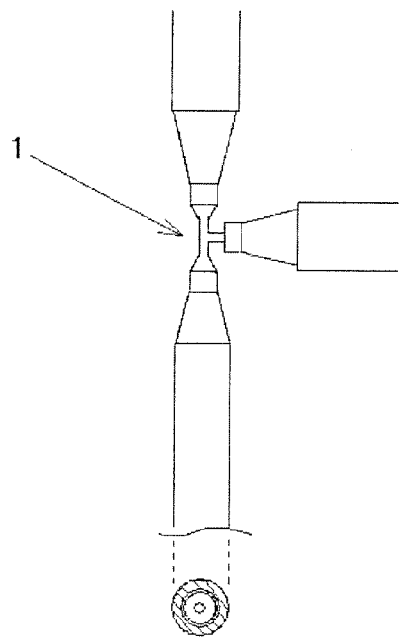
FIG. 1 shows an example of the conceptual diagram illustrating a micromixer used in a microreactor.

DETAILED DESCRIPTION OF THE INVENTION (Method for Producing Fluorine-Containing Substituted Compound)

The method for producing a fluorine-containing substituted compound of the present invention includes introducing into a microreactor provided with a flow path capable of mixing a plurality of liquids an organofluorine compound, an organolithium compound, and an electrophile exhibiting electrophilic effect on the reaction product between the organofluorine compound and the organolithium compound, under the conditions of the temperature being −55° C. or higher, and if necessary, other steps.

According to the method for producing a fluorine-containing substituted compound, the precise flow control, the detailed temperature control and the rapid mixing of the reaction solutions can be realized with the aid of a microreactor, and hence the fluorine-containing substituted compound can be efficiently produced under industrially practicable temperature conditions.

As another Embodiment, the method for producing a fluorine-containing substituted compound of the present invention includes: introducing an organofluorine compound and an organolithium compound into a microreactor provided with a flow path capable of mixing a plurality of liquids, to thereby obtain a reaction product; introducing, into the microreactor, the reaction product and an electrophile exhibiting electrophilic effect on the reaction product, to thereby obtain a fluorine-containing substituted compound; and other steps, if necessary.

According to the method for producing a fluorine-containing substituted compound, the precise flow control, the detailed temperature control and the rapid mixing of the reaction solutions can be realized with the aid of a microreactor, and hence it is possible to directly form a reaction product (active species), hitherto regarded as impossible to form, without the concomitant presence of any electrophile; by subsequently allowing a highly reactive electrophile and the reaction product to react with each other, the yield of the fluorine-containing substituted compound that is low in yield when produced with a conventional production method can be improved; and a novel fluorine-containing substituted compound that cannot be produced with a conventional production method can be produced efficiently.

<Step of Introducing into Microreactor, Step of Obtaining Reaction Product and Step of Obtaining Fluorine-Containing Compound>

In the method for producing a fluorine-containing substituted compound of the present invention, the organofluorine compound, the organolithium compound and the electrophile are introduced into a microreactor provided with a flow path capable of mixing a plurality of liquids.

The organofluorine compound, each of the organolithium compound and the electrophile is usually introduced into the microreactor in a state of being a liquid prepared by solubilization thereof in a solvent. In an aspect, the organofluorine compound, the organolithium compound and the electrophile are each solubilized in a solvent, and the resulting solutions are introduced from separate flow paths. In another aspect, the solution prepared by solubilizing the organofluorine compound and the electrophile and the solution prepared by solubilizing the organolithium compound are introduced from separate flow paths. Here, as the introduction method, for example, syringe pumps can be used as described below.

The organofluorine compound, the organolithium compound and the electrophile having been introduced into the microreactor are mixed in the microreactor.

The use of the microreactor allows the organofluorine compound, the organolithium compound and the electrophile to be efficiently mixed to result in no waste of the materials used, and thus, it is facilitated to efficiently produce the fluorine-containing substituted compound by successively and continuously adding reaction materials.

Also, by using the microreactor, the heat of reaction can be efficiently removed, and hence the temperature unevenness in the reaction solution vanishes and the side reactions can be suppressed.

Here, the embodiment of the introduction and the mixing is described with reference to FIG. 1. The mixing is performed by the micromixer 1 constituting the microreactor. For example, from the vertical tubes (flow paths) connected to the micromixer 1, the solution of the organofluorine compound and the solution of the organolithium compound are respectively introduced. The introduced solutions are mixed in the micromixer 1, and flow into the tube in the right direction, and the above-described reaction occurs in the tube.

In the micromixer, the portion (outlet portion) into which no solutions are introduced is the lowest in pressure, the solutions flow in the direction of the lowest pressure (in the right direction in FIG. 1), and hence usually a problem such as counter flow does not occur.

By mixing the organofluorine compound, the organolithium compound and the electrophile, the following reaction occurs in the microreactor.

In the case where the organofluorine compound, the organolithium compound and the electrophile are introduced into the microreactor (the system in the concomitant presence of the electrophile), and the reactivity of the organofluorine compound to the organolithium compound is higher than the reactivity of the electrophile to the organolithium compound, and in the case where only the organofluorine compound and the organolithium compound are introduced into the microreactor (the system without the concomitant presence of the electrophile), it is considered that the organofluorine compound and the organolithium compound first undergo the halogen-lithium exchange reaction in the microreactor.

The halogen-lithium exchange reaction is represented by the following reaction formula:

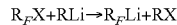

In this formula, R represents an organic group, $R_F$ represents a fluorine-containing organic group, and X represents a halogen atom other than a fluorine atom.

The reaction product obtained by the foregoing reaction is a lithium complex having as a ligand a fluorine-substituted carbene (also referred to as a fluorine-substituted carbene complex or a fluorine-substituted carbenoid); many of such complexes exhibit high radical reactivity similarly to carbene.

Next, by allowing the reaction product and the electrophile having the electrophilic effect on the reaction product to react with each other, a fluorine-containing organic group is inserted into the molecule of the electrophile, and thus, the fluorine-containing substituted compound can be obtained.

On the other hand, in the concomitant presence of the electrophile, when the reactivity of the electrophile to the organolithium compound is higher than the reactivity of the organofluorine compound to the organolithium compound, the halogen-lithium exchange reaction hardly occurs, and hence the yield of the target fluorine-containing substituted compound is low, or the target fluorine-containing substituted compound is not obtained at all. Accordingly, when such an electrophile as described above is used, it is preferable to use a system without the concomitant presence of the electrophile.

As a specific example of the reaction, for example, the specific reaction in the microreactor in the case where a perfluoroalkyl halide is used as the organofluorine compound and butyllithium is used as the organolithium compound is represented by the following reaction formula:

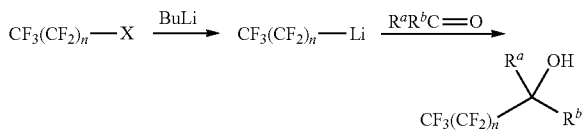

In this formula, X represents a halogen atom other than a fluorine atom, $R^a$ represents an organic group, $R^b$ represents a hydrogen atom or an organic group, and n is an integer of 1 or more.

Hereinafter, the microreactor, the organofluorine compound, the organolithium compound and the electrophile used in the method for producing a fluorine-containing substituted compound of the present invention are described in detail.

<<Microreactor>>

The microreactor is provided with a minute flow path capable of mixing a plurality of liquids, and if necessary, provided with an introduction path communicatively connected to the flow path so as to introduce a liquid into the foregoing flow path, and if necessary, further includes a constitution other than the flow path and the introduction path.

The microreactor is not particularly limited as long as the microreactor is provided with a minute flow path capable of mixing a plurality of liquids; the microreactor can be appropriately selected according to the intended purpose; thus, examples of such a microreactor include a micromixer (such as a board-type micromixer and a tube fitting-type micromixer) and a branched tube.

The board-type micromixer includes a board inside which or on the surface of which flow paths are formed, and is sometimes referred to as a microchannel.

The board-type micromixer is not particularly limited as long as not impairing the advantageous effects of the present invention, and can be appropriately selected according to the intended purpose; examples of such a board-type micromixer include a mixer having a fine flow path for mixing, described in International Publication No. WO/96/30113 pamphlet, and mixers described in a literature, "Microreactors," Chapter 3, by W. Ehrfeld, V. Hessel, H. Lowe, published by Wiley-VCH.

The board-type micromixer preferably includes as formed therein, in addition to the flow path, one or more introduction paths, communicatively connected to the flow path, introducing a plurality of liquids into the flow path. In other words, a constitution is preferable in which the upstream portion of the flow path is branched according to the number of the introduction paths.

The number of the introduction paths is not particularly limited, and can be appropriately selected according to the intended purpose; it is preferable to introduce a plurality of liquids intended to be mixed with each other from separate introduction paths, and to merge and mix the liquids in the flow path. Alternatively, a constitution may also be adopted in which one liquid may be beforehand placed in the flow path, and the other liquids are introduced from the introduction paths.

The tube fitting-type micromixer is provided with a flow path formed inside thereof, and provided with one or more connecting units for connecting the flow path formed inside the micromixer and one or more tubes (see, FIG. 1). The connection mode in each of the connecting units is not particularly limited, and can be appropriately selected from among the heretofore known tube connection modes according to the intended purpose; examples of the mode of such a connection unit include screwed type, union type, butt welding type, slip-on welding type, socket welding type, flanged type, flareless type and mechanical type.

The inside of the tube fitting-type micromixer preferably includes as formed therein in addition to the flow path, one or more introduction paths, communicatively connected to the flow path, introducing a plurality of liquids into the flow path. In other words, a constitution is preferable in which the upstream portion of the flow path is branched according to the number of the introduction paths. When the number of the introduction paths is two, for example, a T-shaped or Y-shaped micromixer can be used as the tube fitting-type micromixer; when the number of the introduction paths is three, for example, a cross-shaped micromixer can be used as the tube fitting-type micromixer. Alternatively, a constitution may also be adopted in which one liquid may be beforehand placed in the flow path, and the other liquids are introduced from the introduction paths.

The material for the micromixer is not particularly limited, and can be appropriately selected according to the requirements involving the factors such as heat resistance, pressure resistance, solvent resistance and easiness in processing; examples of such a material include: stainless steel, titanium, copper, nickel, aluminum, silicon and fluororesins such as Teflon (registered trademark) and PFA (perfluoroalkoxy resin) and TFAA (trifluoroacetamide).

The micromixer precisely controls the flow of the reaction solution through the microstructure thereof, and hence is preferably fabricated with microfabrication technique.

The microfabrication technique is not particularly limited, and can be appropriately selected according to the intended purpose; examples of such a microfabrication technique include: (a) LIGA technique as a combination of X-ray lithography and electroplating, (b) a high aspect ratio photolithography method using EPON SU8, (c) a mechanical micro-machining (such as a micro drill machining by high-speed rotation of a drill having a drill diameter of the order of microns), (d) a high aspect ratio processing of silicon by Deep RIE, (e) Hot Emboss processing, (f) a laser beam lithography, (g) a laser processing and (h) an ion beam method.

As the micromixer, commercial products can be used; examples of such a commercial product include: a microreactor provided with interdigital channel structure; a single mixer and a caterpillar mixer manufactured by Institut fur Mikrotechnik Mainz (IMM) GmbH; a micro-glass reactor manufactured by Mikroglas Chemtech GmbH; Cytos manufactured by CPC Systems GmbH; Model YM-1 mixer and Model YM-2 mixer manufactured by Yamatake Corp.; Mixing Tee and Tee (T-shaped connector) manufactured by Shimadzu GLC Ltd.; IMT chip reactor manufactured by Institute of Microchemical Technology Co., Ltd; Micro High Mixer developed by Toray Engineering Co., Ltd.; Union Tee manufactured by Swagelok Co.; and a T-shaped micromixer manufactured by Sankoh Seiki Kogyo Co., Ltd.

As the microreactor, the micromixer may be used alone, or alternatively, the micromixer may have a constitution in which a tube reactor is connected downstream of the micromixer so as to extend the flow path. The connection of the tube reactor downstream of the micromixer enables the regulation of the flow path length. The residence time (reaction time) of the mixed liquid is proportional to the length of the flow path.

The tube reactor is a reactor for the detailed control (the residence time control) of the time required for performing the subsequent reaction of the solution rapidly mixed in the micromixer.

The tube reactor is not particularly limited; for example, the constitution including inner diameter, outer diameter, length and material of the tube can be appropriately selected according to the intended reaction.

As the tube reactor, commercial products can be used; examples of such a commercial product include: a stainless steel tube (outer diameter: $\frac{1}{16}$ (1.58 mm); inner diameter: selectable from 250 μm, 500 μm and 1,000 μm; length: adjustable by the user) manufactured by GL Sciences Inc.

The material of the tube reactor is not particularly limited; the materials quoted as the examples of the materials for the micromixer can also be suitably used.

The residence time t in the tube reactor is preferably 0.01 sec to 10 sec, more preferably 0.05 sec to 5.0 sec and particularly preferably 0.10 sec to 1.0 sec.

When the residence time is less than 0.01 sec, sometimes no sufficient reaction occurs; when the residence time exceeds 10 sec, sometimes the decomposition reaction of the lithium intermediate (fluorine-substituted lithium carbenoid) proceeds.

—Flow Path—

The flow path has a function to mix a plurality of liquids by diffusion, and a function to remove the heat of reaction.

The mixing method of the liquid in the flow path is not particularly limited, and can be appropriately selected according to the intended purpose; examples of such a mixing method include a mixing based on laminar flow and a mixing based on turbulence. Among such mixing methods, the mixing based on laminar flow (static mixing) is preferable because the mixing based on laminar flow allows the reaction control or the removal of heat to be performed more efficiently.

The flow path in the microreactor is minute, and hence the plurality of liquids introduced from the introduction path mutually tend to spontaneously form a flow governed by laminar flow, and diffuse in the direction perpendicular to the flow to be mixed with each other. In the mixing based on laminar flow, a constitution may also be adopted in which the mixing rate is increased by adopting a constitution in which by further providing a branching point and a merging point in the flow path, the cross-section of the flowing liquid is divided.

When the mixing based on turbulence (dynamic mixing) is performed in the flow path of the microreactor, the flow can be changed over from laminar flow to turbulence by regulating the flow rate or the flow path shape (for example, the three-dimensional shape of the liquid contact portion, the shape of the flow path such as the bending of the flow path, and the roughness of the wall surface). The mixing based on turbulence has an advantage such that the mixing efficiency is better and the mixing rate is faster as compared to the mixing based on laminar flow.

In this connection, the smaller inner diameter of the flow path can make shorter the diffusion length of the molecules, and hence can reduce the time required for mixing and can improve the mixing efficiency. Further, the smaller inner diameter of the flow path increases the ratio of the surface area to the volume, and hence, for example, facilitates the performance of the temperature control of the liquid such as the removal of the heat of reaction.

On the other hand, when the inner diameter of the flow path is too small, the pressure loss when a liquid is allowed to flow is increased, and as the pump used for liquid transfer, a specific pump having a high pressure resistance is required and thus the production cost is sometimes increased. Additionally, when the flow rate in the liquid transfer is limited, the structure of the micromixer is sometimes limited.

The inner diameter of the flow path is not particularly limited as long as not impairing the advantageous effects of the present invention, and can be appropriately selected according to the intended purpose; however, the inner diameter of the flow path is preferably 50 µm to 4 mm, more preferably 100 µm to 3 mm, furthermore preferably 250 µm to 2 mm and particularly preferably 500 µm to 1 mm.

When the inner diameter is less than 50 µm, the pressure loss is sometimes increased. When the inner diameter exceeds 4 mm, the surface area per unit volume becomes small, and consequently, rapid mixing or the removal of the heat of reaction becomes sometimes difficult. On the other hand, the inner diameter falling within the foregoing particularly preferable range is advantageous in that mixing can be performed more rapidly and the heat of reaction can be more efficiently removed.

More specifically, the inner diameter of the flow path formed inside the micromixer is preferably 50 µm to 1,000 µm, more preferably 100 µm to 800 µm, and furthermore preferably 250 µm to 500 µm. The inner diameter of the tube reactor connected downstream of the micromixer is preferably 50 µm to 4 mm, more preferably 100 µm to 2 mm and furthermore preferably 500 µm to 1 mm.

The cross-sectional area of the flow path is not particularly limited, and can be appropriately selected according to the intended purpose; the cross-sectional area of the flow path is preferably 100 µm$^2$ to 16 mm$^2$, more preferably 1,000 µm$^2$ to 4.0 mm$^2$, furthermore preferably 10,000 µm$^2$ to 2.1 mm$^2$ and particularly preferably 190,000 µm$^2$ to 1 mm$^2$.

The length of the flow path is not particularly limited, and can be appropriately regulated according to the optimum reaction time; however the length of the flow path is preferably 0.1 m to 3 m and more preferably 0.5 m to 2 m.

The cross-sectional shape of the flow path is not particularly limited, and can be appropriately selected according to the intended purpose; examples of the cross-sectional shape of the flow path include a circular shape, a rectangular shape, a semicircular shape and a triangular shape.

—Introduction Path—

The introduction paths are communicatively connected to the flow path, and each have a function to introduce the liquid in the introduction path concerned into the flow path. In each of the introduction paths, the end of the introduction path other than the end communicatively connected to the flow path is connected to the vessel that contains a liquid intended to be mixed.

The inner diameters of the introduction paths are not particularly limited as long as not impairing the advantageous effects of the present invention, and can be appropriately selected according to the intended purpose; however, the inner diameters of the introduction paths are preferably 500 µm or less and more preferably 250 µm or less. When the microreactor has a plurality of introduction paths, the inner diameters of the respective introduction paths may be different from each other, or may be the same as each other.

—Constitution Other than Flow Path and Introduction Path(s)—

The constitution other than the flow path and the introduction path(s) is not particularly limited and can be appropriately selected according to the intended purpose; for example, the constitution concerned may include a pump used for liquid transfer, a temperature regulation unit, a reaction promotion unit, a sensor and a tank for storing the produced polymer.

The pump is not particularly limited, and can be appropriately selected from the industrially usable pumps; however, those pumps which do not cause pulsation at the time of liquid transfer are preferable, and examples of such a pump include a plunger pump, a gear pump, a rotary pump and a diaphragm pump.

<<Temperature>>

When the reaction is performed in the concomitant presence of the electrophile, the reaction temperature T in the reaction is not particularly limited, and can be appropriately selected according to the intended purpose; the reaction temperature T applied in the conventional batch type reaction, namely, a temperature of −78° C. or lower can be applied; however, in the present invention, such a temperature of −55° C. or higher that cannot be adopted in conventional methods can be applied.

Such a temperature is preferably −55° C. or higher, more preferably −20° C. or higher and particularly preferably 0° C. or higher. The temperature being −55° C. or higher is preferable in that the fluorine-containing substituted compound can be produced by using a cooling apparatus having a simple construction and the production cost can be reduced.

The temperature being 0° C. or higher is preferable in that the fluorine-containing substituted compound can be produced by using a cooling apparatus having a simpler construction and the production cost can be reduced drastically. The temperature is not restricted by a particular upper limit, but may be set usually at 100° C. or lower, preferably at 50° C. or lower and more preferably at 25° C. or lower. The temperature exceeding 25° C. requires heating, and hence the temperature being 25° C. or lower is preferable from the viewpoint of the production cost.

When the reactivity of the electrophile to the organolithium compound is higher than the reactivity of the organofluorine compound to the organolithium compound, the use of the system without the concomitant presence of the electrophile is preferable in that the electrophile does not inhibit the halogen-lithium exchange reaction, and the yield of the target fluorine-containing substituted compound can be improved.

In the system without the concomitant presence of the electrophile, the temperature T is preferably −100° C. or higher. When the temperature T is lower than −100° C., the precise temperature control sometimes becomes difficult and the production cost is sometimes increased. On the other hand, when the temperature T falls within the preferable range, such a temperature is industrially practicable, and the fluorine-containing substituted compound can be produced with a simple apparatus and simple operations.

When the organofluorine compound and the organolithium compound are allowed to react with each other in the system without the concomitant presence of the electrophile, in the case where the organofluorine compound is a fluoroalkyl halide having 6 carbon atoms, from the viewpoint of the yield of the fluorine-containing substituted compound, the relation in the reaction between the temperature T (° C.) and the residence time t (sec) of the solution in the flow reactor satisfies preferably the following relation (1), more preferably the following relation (2) and furthermore preferably the following relation (3).

$$T \leq -3.8t-48 \quad \text{Relation (1)}$$

$$T \leq -6.5t-55 \quad \text{Relation (2)}$$

$$T \leq -11t-57 \quad \text{Relation (3)}$$

The temperature T (° C.) and the residence time t (sec) particularly preferably satisfy either of the following relations (i) and (ii).

$$-78 \leq T \leq -68, \text{ and } 0.25 \leq t \leq 0.52 \quad \text{(i)}$$

$$T = -78, \text{ and } 0.15 \leq t \leq 0.25 \quad \text{(ii)}$$

In the case where the organofluorine compound is a fluoroalkyl halide having 2 carbon atoms, the temperature T (° C.) and the residence time t (sec) preferably satisfy the relations $-100 \leq T \leq 0$, and $0.15 \leq t \leq 8.4$.

In the case where the organofluorine compound is a fluoroalkyl halide having 3 carbon atoms, the following relation (4) is preferably satisfied; in the case where the organofluorine compound is a fluoroalkyl halide having 4 carbon atoms, the following relation (5) is preferably satisfied; and in the case where the organofluorine compound is a fluoroalkyl halide having 5 carbon atoms, the following relation (6) is preferably satisfied.

$$T \leq -3.2t-45 \quad \text{Relation (4)}$$

$$T \leq -5.1t-47 \quad \text{Relation (5)}$$

$$T \leq -7.1t-47 \quad \text{Relation (6)}$$

<<Organofluorine Compound>>

The organofluorine compound is not particularly limited as long as the organofluorine compound produces the reaction product as an active species (radical) through the reaction with the organolithium compound, and can be appropriately selected according to the intended purpose. In general, preferably the halogen-lithium exchange reaction occurs between the organofluorine compound and the organolithium compound to produce a highly reactive fluorine-substituted carbenoid; examples of the organofluorine compound to form the fluorine-substituted carbenoid include fluorine-substituted alkyl halide (also referred to as "fluoroalkyl halide" and inclusive of perfluoroalkyl halide).

The fluoroalkyl halide is not particularly limited and can be appropriately selected according to the intended purpose, and is preferably the fluoroalkyl halide represented by the following general formula (a1) or the fluoroalkyl vinyl halide represented by the following general formula (a2).

$$C_j H_k F_l X_m \quad \text{General Formula (a1)}$$

In the general formula (a1), X represents a halogen atom other than a fluorine atom, j, k, l and m satisfy the relation $2j+2=k+l+m$, where j is an integer of 1 to 20, k is an integer of 0 or more, and l and m are each an integer of 1 or more. Preferably, j is an integer of 1 to 10.

General Formula (a2)

$$Y-\underset{\underset{CH_2}{\|}}{C}-C_j H_k F_l X_m$$

In the general formula (a2), X and Y may be the same as or different from each other and each represent a halogen atom other than a fluorine atom, j, k, l and m satisfy the relation $2j+2=k+l+m$, where j is an integer of 1 to 20, k is an integer of 0 or more, and l and m are each an integer of 1 or more. Preferably, j is an integer of 1 to 10.

Examples of the fluoroalkyl halide represented by the general formula (a1) include tribromofluoromethane, dibromodifluoromethane, bromochlorodifluoromethane, bromotrifluoromethane, trichlorofluoromethane and 1,2-dibromotetrafluoroethane.

Examples of the fluoroalkyl vinyl halide represented by the general formula (a2) include 1-(trifluoromethyl)vinyl bromide, 1-(bromodifluoromethyl)vinyl bromide, 1-(dibromofluoromethyl)vinyl bromide, 1-(pentafluoroethyl)vinyl bromide and 1-(heptafluoropropyl)vinyl bromide.

The perfluoroalkyl halide is not particularly limited and can be appropriately selected according to the intended purpose, and is preferably the perfluoroalkyl halide represented by the following general formula (b).

$$C_n F_{2n+1} X \quad \text{General Formula (b)}$$

In the general formula (b), X represents a halogen atom other than a fluorine atom, n is an integer of 1 to 20 and preferably an integer of 1 to 10.

Examples of the perfluoroalkyl halide represented by the general formula (b) include perfluoroalkyl iodide and perfluoroalkyl bromide.

Examples of the perfluoroalkyl iodide include iodopentafluoroethane, heptafluoropropyl iodide, nonafluorobutyl iodide, undecafluoropentyl iodide and tridecafluorohexyl iodide.

Examples of the perfluoroalkyl bromide include pentafluoroethyl bromide, heptafluoropropyl bromide, nonafluorobutyl bromide, undecafluoropentyl bromide and tridecafluorohexyl bromide.

These organofluorine compounds may be used each alone or in combinations of two or more thereof.

The molar concentration of the organofluorine compound at the time of the introduction into the microreactor is not particularly limited and can be appropriately selected according to the intended purpose, and is preferably 0.01 M to 4.0 M (M: mol/L, the same shall apply hereinafter), more preferably 0.05 M to 3.0 M and particularly preferably 0.10 M to 2.0 M.

When the concentration is less than 0.01 M, the formation amount of the fluorine-containing substituted compound per unit time is sometimes decreased. When the concentration exceeds 4.0 M, the removal of the heat of reaction is sometimes insufficient.

The flow rate of the introduction of the organofluorine compound from the introduction path of the microreactor is not particularly limited and can be appropriately selected according to the intended purpose, and is preferably 0.10 mL/min to 50 mL/min, more preferably 0.50 mL/min to 25 mL/min and particularly preferably 1.0 mL/min to 10 mL/min.

When the flow rate is less than 0.10 mL/min, no rapid mixing is sometimes realized; and when the flow rate exceeds 50 mL/min, the pressure loss is large and sometimes the yield of the fluorine-containing substituted compound is adversely affected.

<<Organolithium Compound>>

The organolithium compound is not particularly limited and can be appropriately selected according to the type of the organofluorine compound and the type of the electrophile; examples of the organolithium compound include alkyllithium, benzyllithium, alkenyllithium, alkynyllithium, aralkyllithium, aryllithium, heterocyclic lithium compounds and alkyl lithium magnesium complex.

Examples of the alkyllithium include methyllithium, ethyllithium, propyllithium, butyllithium (such as n-butyllithium, sec-butyllithium, iso-butyllithium or tert-butyllithium), pentyllithium, hexyllithium, methoxymethyllithium and ethoxymethyllithium.

Examples of the benzyllithium include benzyllithium, α-methylstyryllithium, 1,1-diphenyl-3-methylpentyllithium and 1,1-diphenylhexyllithium.

Examples of the alkenyllithium include vinyllithium, allyllithium, propenyllithium and butenyllithium.

Examples of the alkynyllithium include ethynyllithium, butynyllithium, pentynyllithium and hexynyllithium.

Examples of the aralkyllithium include phenylethyllithium.

Examples of the aryllithium include phenyllithium and naphthyllithium.

Examples of the heterocyclic lithium compound include 2-thienyllithium, 4-pyridyllithium and 2-quinolyllithium.

Examples of the alkyl lithium magnesium complex include tri(n-butyl)magnesium lithium and trimethylmagnesium lithium.

These may be used each alone or in combinations of two or more thereof.

The organolithium compound may be an ate complex including an atom of a metal such as copper, zinc or aluminum.

As the organolithium compound, butyllithium is preferable because any one of the isomers different in reactivity such as n(primary)-butyllithium, sec(secondary)-butyllithium and tert(tertiary)-butyllithium is commercially available as a solution in a hydrocarbon such as hexane so as to be easily accessible, and such hydrocarbon solutions are stable at room temperature over a long period of time and are easy to use.

The molar concentration of the organolithium compound is not particularly limited and can be appropriately selected according to the type and the concentration of the organofluorine compound, and is preferably 0.001 M to 3.0 M, more preferably 0.005 M to 0.75 M and particularly preferably 0.01 M to 0.50 M.

When the concentration is less than 0.001 M, the organolithium compound is decomposed, for example, by the water contained in the solvent, and when the concentration exceeds 3.0 M, the solubility of the organolithium compound sometimes causes a problem.

The flow rate of the introduction of the organolithium compound from the introduction path of the microreactor is not particularly limited and can be appropriately selected according to the intended purpose, and is preferably 0.10 mL/min to 10 mL/min, more preferably 0.50 mL/min to 5.0 mL/min and particularly preferably 1.0 mL/min to 3.0 mL/min.

When the flow rate is less than 0.10 mL/min, no rapid mixing is realized, and the yield of the fluorine-containing substituted compound is sometimes decreased; when the flow rate exceeds 10 mL/min, the pressure loss cannot be suppressed, and the yield of the fluorine-containing substituted compound is sometimes decreased.

<<Electrophile>>

The electrophile is not particularly limited as long as the electrophile has the electrophilic effect on the reaction product between the organofluorine compound and the organolithium compound and can be appropriately selected according to the intended purpose. Whether or not the electrophile has the electrophilic effect is relatively determined by the relation with the reaction product, and cannot be said sweepingly, but examples of the compound tending to have the electrophilic effect include aldehydes, ketones, isocyanates, tin compounds and silyl compounds.

The reaction product is the foregoing reaction product between the organofluorine compound and the organolithium compound, and specifically, a lithium complex (fluorine-substituted lithium carbenoid) having as a ligand a fluorine-substituted carbene.

The aldehydes are not particularly limited as long as the aldehydes each have an aldehyde group, and examples of the aldehydes include: aliphatic aldehydes, which may have a substituent(s), having 2 to 10 carbon atoms; aromatic aldehydes, which may have a substituent(s), having 4 to 20 carbon atoms; and heterocyclic aldehydes, which may have a substituent(s), having 4 to 20 carbon atoms. The substituent is not particularly limited as long as the substituent adversely affects the reaction; examples of such a substituent include alkyl group having 1 to 4 carbon atoms and a phenyl group.

Specific compound examples of the aldehydes include acetaldehyde, propionaldehyde, isobutylaldehyde, n-butylaldehyde, isovaleraldehyde, n-valerylaldehyde, n-hexanealdehyde and benzaldehyde.

The ketones are not particularly limited as long as the ketones each have a ketone group, and examples of the ketones include: aliphatic ketones, which may have a substituent(s), having 2 to 10 carbon atoms; aromatic ketones, which may have a substituent(s), having 4 to 20 carbon atoms; and heterocyclic ketones, which may have a substituent(s), having 4 to 20 carbon atoms. The substituent is not particularly limited as long as the substituent adversely affects the reaction; examples of such a substituent include alkyl group having 1 to 4 carbon atoms and a phenyl group.

Specific compound examples of the ketones include methyl ethyl ketone, diethyl ketone, methyl isobutyl ketone, cyclohexanone and acetophenone. Chlorosilanes and silaketones in which the carbon atoms in the main chain are replaced with silicon atoms can also be used.

The isocyanates are not particularly limited as long as the isocyanates each have an isocyanate group, and examples of the isocyanates include aliphatic isocyanates, which may have a substituent(s), having 2 to 10 carbon atoms; aromatic isocyanates, which may have a substituent(s), having 4 to 20 carbon atoms; and heterocyclic isocyanates, which may have a substituent(s), having 4 to 20 carbon atoms. The substituent is not particularly limited as long as the substituent adversely affects the reaction; examples of such a substituent include alkyl group having 1 to 4 carbon atoms and a phenyl group.

Specific compound examples of the isocyanates include methyl isocyanate, ethyl isocyanate, propyl isocyanate, n-butyl isocyanate, tert-butyl isocyanate, phenyl isocyanate, tolylenediisocyanate and hexamethylenediisocyanate.

Among these, benzaldehyde and n-butylisocyanate are preferable because the halogen-lithium exchange reaction between the organofluorine compound and the organolithium compound is not inhibited, and the reactivity with the reaction product is high.

Examples of the tin compound include the compounds represented by the following general formula (c).

General Formula (c)

In the general formula (c), $R^5$ to $R^7$ may be the same as or different from each other, and each represent an aliphatic group, which may have a substituent(s), having 1 to 9 carbon atoms; an aromatic group, which may have a substituent(s), having 3 to 19 carbon atoms or a heterocyclic group, which may have a substituent(s), having 3 to 19 carbon atoms; and $X^2$ represents Cl, Br or I.

Specific examples of the tin compound include tributyltin chloride and triphenyltin chloride.

Examples of the silyl compound include the compounds represented by the general formula (d).

General Formula (d)

In the general formula (d), $R^8$ to $R^{10}$ may be the same as or different from each other, and each represent an aliphatic group, which may have a substituent(s), having 1 to 9 carbon atoms; an aromatic group, which may have a substituent(s), having 3 to 19 carbon atoms or a heterocyclic group, which may have a substituent(s), having 3 to 19 carbon atoms; and $X^3$ represents Cl, Br, I or Tf (Tf represents a trifluoromethylsulfonyl group).

Specific examples of the silyl compound include trimethylsilyl trifluoromethanesulfonate and trimethylsilyl iodide.

The foregoing electrophiles may be used each alone or in combinations of two or more thereof.

The molar concentration of the electrophile at the time of the introduction into the microreactor is not particularly limited and can be appropriately selected according to the intended purpose, and is preferably 0.01 M to 4.0 M, more preferably 0.05 M to 3.0 M and particularly preferably 0.10 M to 2.0 M.

When the concentration is less than 0.01 M, the formation amount of the fluorine-containing substituted compound per unit time is sometimes decreased. When the concentration exceeds 4.0 M, the removal of the heat of reaction is sometimes insufficient.

The relations between the molar concentration of the electrophile, the molar concentration of the organofluorine compound and the molar concentration of the organolithium compound are not particularly limited and can be appropriately selected according to the intended purpose; however, preferably the molar concentrations each fall within the foregoing preferable range from the viewpoint of, for example, the solubility, the viscosity and the removal of the heat of reaction.

The flow rate of the introduction of the electrophile from the introduction path of the microreactor is not particularly limited and can be appropriately selected according to the intended purpose, and is preferably 0.10 mL/min to 50 mL/min, more preferably 0.50 mL/min to 25 mL/min and particularly preferably 1.0 mL/min to 10 mL/min.

When the flow rate is less than 0.10 mL/min, no rapid mixing is sometimes realized; when the flow rate exceeds 50 mL/min, the pressure loss is large, and the yield of the fluorine-containing substituted compound is sometimes affected.

The relation between the flow rate of the introduction of the electrophile into the microreactor and the flow rate of the introduction of the methyllithium (reaction product) into the microreactor is not particularly limited and can be appropriately selected according to the intended purpose; however, preferably the flow rates each fall within the foregoing preferable range from the viewpoint of, for example, the viscosity and the removal of the heat of reaction.

In this connection, the present inventors have revealed that in the production of the fluorine-containing substituted compound using the microreactor, the equivalence ratio between the organofluorine compound, the organolithium compound and the electrophile coincides with the ratio between the product of the concentration and the flow rate of the organofluorine compound, the product of the concentration and the flow rate of the organolithium compound and the product of the concentration and the flow rate of the electrophile.

The equivalence ratio between the organofluorine compound and the electrophile is not particularly limited and can be appropriately selected according to the intended purpose; in relation to the organofluorine compound, the amount of the electrophile is preferably 1.0 equivalent to 20 equivalents, more preferably 1.0 equivalent to 5.0 equivalents and particularly preferably 1.0 equivalent to 2.0 equivalents. When the equivalence ratio is less than 1.0 equivalent, the yield of the fluorine-containing substituted compound is decreased; when the equivalence ratio exceeds 20 equivalents, the electrophile is excessive in relation to the reaction product, and the yield of the fluorine-containing substituted compound is sometimes decreased.

The equivalence ratio between the organofluorine compound and the organolithium compound is not particularly limited, and can be appropriately selected according to the intended purpose; in relation to the organofluorine compound, the amount of the organolithium compound is preferably 0.5 equivalent to 5.0 equivalents and more preferably 1.0 equivalent to 3.0 equivalents.

When the equivalence ratio is less than 0.5 equivalent, the halogen-lithium exchange reaction sometimes does not proceed sufficiently; when the concentration is 5.0 equivalents or more, the organolithium compound is excessive in relation to the organofluorine compound, and the production cost is increased.

—Solvents—

The organofluorine compound, the organolithium compound and the electrophile are each preferably introduced into the microreactor in a liquid state of being solubilized in a solvent. The organofluorine compound and the electrophile may also be mixed and then solubilized in a solvent.

The solvent is not particularly limited, and can be appropriately selected according to the types of the organofluorine compound, the organolithium compound and the electrophile.

Examples of the solvent include hydrocarbon-based solvents and ether-based solvents; more specifically, examples of the hydrocarbon-based solvents include n-pentane, n-hexane, n-heptane, n-octane, iso-octane, cyclohexane, benzene, toluene, xylene, decalin, tetralin, and the derivatives of these; and examples of the ether-based solvents include diethyl ether, tetrahydrofuran (THF), 1,4-dioxane, 1,2-dimethoxyethane, diethylene glycol dimethyl ether and diglyme. Among these, diethyl ether is preferable from the viewpoint of the solubility of the organofluorine compound, the strength of the solvation of the counter cation and the satisfactory yield.

For the purpose of being coordinated to the counter cation to increase the steric hindrance, an amine compound or a cyclic ether may also be added in a small amount to the solvent.

Examples of the amine compound include triethylamine, N,N-dimethylaniline, pyridine, N,N,N',N'-tetramethylethylenediamine (TMEDA) and N,N,N',N',N'',N''-hexamethylphosphoric triamide (RMPA); examples of the cyclic ether include crown ether.

<Other Steps>

The other steps are not particularly limited, and can be appropriately selected according to the intended purpose; examples of such other steps include a step of further continuously introducing the fluorine-containing substituted compound and methanol into the microreactor. The step concerned is a step for continuously performing methanol quenching by introducing methanol into the microreactor further provided with a micromixer and a flow reactor downstream of the flow reactor in which the fluorine-containing substituted compound is produced. By performing the foregoing step in the microreactor, the high speed mixing, the detailed temperature control and the detailed residence time control in the methanol quenching are realized and thus the yield of the fluorine-containing substituted compound can be improved.

The flow rate of methanol is not particularly limited, and can be appropriately selected according to the intended purpose; however, the flow rate of methanol is preferably 0.10 mL/min to 50 mL/min, more preferably 0.50 mL/min to 25 mL/min and particularly preferably 1.0 mL/min to 10 mL/min.

When the flow rate is less than 0.10 mL/min, the rapid mixing is not realized and the yield of the fluorine-containing substituted compound is sometimes decreased; when the flow rate exceeds 50 mL/min, the pressure loss is sometimes increased.

The residence time in the methanol quenching is preferably 0.10 sec to 30 sec, more preferably 0.50 sec to 10 sec and particularly preferably 1.0 sec to 5.0 sec.

When the residence time is less than 0.10 sec, no sufficient quenching is sometimes realized, and when the residence time exceeds 30 sec, the pressure loss is sometimes large.

(Fluorine-Containing Substituted Compound)

The fluorine-containing substituted compound of the present invention is a novel fluorine-containing substituted compound represented by any one of the following general formulas (1) to (10), and is produced by the method for producing a fluorine-containing substituted compound of the present invention.

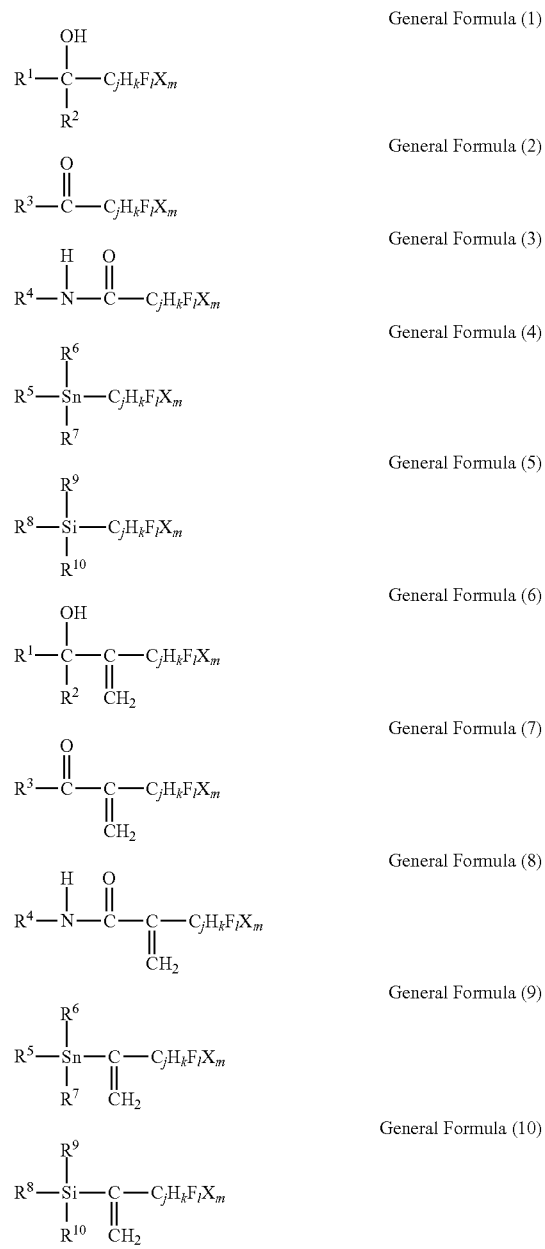

In the general formulas (1) to (10), $R^1$ and $R^3$ to $R^{10}$ may be the same as or different from each other, and each represent an aliphatic group, which may have a substituent(s), having 1 to 9 carbon atoms, an aromatic group, which may have a substituent(s), having 3 to 19 carbon atoms or a heterocyclic group, which may have a substituent(s), having 3 to 19 carbon atoms; $R^2$ represents a hydrogen atom, an aliphatic group, which may have a substituent(s), having 1 to 9 carbon atoms, an aromatic group, which may have a substituent(s), having 3 to 19 carbon atoms or a heterocyclic group, which may have a substituent(s), having 3 to 19 carbon atoms; X represents a halogen atom other than a fluorine atom; j, k, l and m satisfies the relation 2j+1=k+l+m, where j is an integer of 1 to 20, k and m are each an integer of 0 or more and l is an integer of 1 or more. Preferably, j is an integer of 1 to 10. The substituent in each of $R^1$ and $R^3$ to $R^{10}$ is not particularly limited as long as the substituent adversely affects the reaction; examples of such a substituent include alkyl group having 1 to 4 carbon atoms and a phenyl group.

EXAMPLES

Hereinafter, Examples of the present invention are described; however, the present invention is not limited to these Examples in any way.

Test Example 1

The following test was performed for the purpose of verifying that the fluorine-containing substituted compound was able to be produced when a microreactor was used under the same temperature conditions as in the method for producing a fluorine-containing substituted compound in a conventional batch-type reactor.
<Microreactor>
The microreactor used in present Test Example was constituted with a micromixer composed of a T-shaped tube fitting and a tube reactor connected downstream of the micromixer.
—Micromixer—
As the micromixer (in FIG. 2, denoted by "M1"), a custom-made product manufactured by Sankoh Seiki Kogyo Co., Ltd. was used (it is possible to obtain an equivalent by requesting the production on the basis of the description in present Example). The micromixer used in present Example has inside thereof a first introduction path, a second introduction path and a portion of the flow path with which these introduction paths are merged, and the inner diameters of these introduction paths are the same as each other inside the micromixer. Accordingly, hereinafter, these inner diameters are collectively referred to as "the inner diameter of the micromixer."
—Tube Reactor—
As the tube reactor (in FIG. 2, denoted by "R1"), a stainless steel tube manufactured by GL Sciences Inc. was used. As the liquid transfer pump, a syringe pump Model 11 Plus manufactured by Harvard Apparatus Inc. was used. The regulation of the reaction temperature was performed by submerging the whole of the microreactor in a thermostatic bath.
<Preparation of Solutions to be Introduced into Microreactor>
By diluting $CF_3(CF_2)_5Br$ (tridecafluorohexyl bromide, TCI (Tokyo Chemical Industry Co., Ltd.)) and benzaldehyde (manufactured by Aldrich Corp.) with a mixed solution composed of THF and diethyl ether ($(C_2H_5)_2O$, hereinafter, also denoted by $Et_2O$) (volume ratio: $THF/Et_2O=2/1$), a mixed solution of $CF_3(CF_2)_5Br$ and benzaldehyde having the concentrations of 0.12 M and 0.10 M, respectively, was prepared. By diluting sec-butyllithium (sec-BuLi, manufactured by Kanto Chemical Co., Inc.) with hexane, a 0.40 M sec-butyllithium solution was prepared.
<Reaction Conditions>
The prepared mixed solution of $CF_3(CF_2)_5Br$ and benzaldehyde was introduced from one inlet of the microreactor M1, and the prepared sec-butyllithium solution was introduced from the other inlet of the microreactor. The solutions were each sucked into a gas-tight syringe, and then liquid-transferred into the microreactor by using a syringe pump manufactured by Harvard Apparatus Inc.

Figure 2:
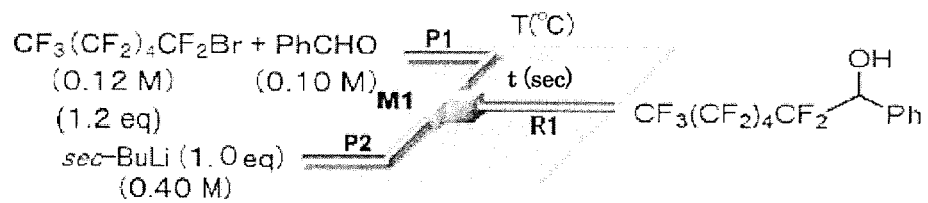
FIG. 2 is a diagram illustrating an outline of the reaction system in Test. Examples 1 to 8.

The solutions were mixed in the micromixer M1, and were allowed to undergo continuous reaction in the tube reactor R1 to produce the fluorine-containing substituted compound (see FIG. 2).

As shown in FIG. 2, the microreactor is constituted with a T-shaped micromixer (M1), a micro tube reactor (R1), and tube reactors (P1, P2) for precooling.

For the micromixer M1, a T-shaped micromixer (micromixer 1, manufactured by Sankoh Seiki Kogyo Co., Ltd., inner diameter: 250 μm, see FIG. 2) was used. For the micro tube reactor and the tube reactor for precooling, a stainless steel tube (outer diameter: 1/16 inch (1.58 mm), inner diameter: 1,000 μm) manufactured by GL Sciences Inc. was used. The residence time can be regulated, not by changing the flow rate, but by changing the length of the stainless steel tube. By submerging the whole of the microreactor in a thermostatic bath, the reaction temperature was set at −78° C.

Into the T-shaped mixer M1, the mixed solution of $CF_3(CF_2)_5Br$ and benzaldehyde and the sec-butyllithium solution were liquid-transferred at the flow rates of 6.00 mL/min and 1.50 mL/min, respectively, by using syringe pumps.

The residence time in the tube reactor R1 (inner diameter: 1,000 μm, length: 50 cm) was set at 3.14 sec.

For each of the tube reactors (P1, P2) for precooling, the inner diameter used was 1,000 μm and the length used was 100 cm.

The mixed reaction solution was discarded for a few minutes until the reaction was stabilized and then taken into a sampling tube for 30 sec.
<Measurement of Yield>
For the obtained reaction solution, the yield of the fluorine-containing substituted compound was determined with an internal standard method using gas chromatography. For the measurement, GC-2014 (manufactured by Shimadzu Corp.) was used. The result thus obtained is shown in Table 1.

Test Examples 2 to 8

In each of Test Examples 2 to 8, the yield of the fluorine-containing substituted compound was measured in the same manner as in Test Example 1 except that in Test Example 1, the type of the organolithium compound, the reaction temperature T (° C.) and the residence time t (sec) in the tube reactor were altered to the combination shown in Table 1. The results thus obtained are shown in Table 1.

The residence time t was altered from 3.14 sec to 12.6 sec by changing the length of the tube reactor from 50 cm to 200 cm.

TABLE 1

| | Organolithium compound | Temperature T (° C.) | Residence time t (sec) | Yield (%) |
|---|---|---|---|---|
| Test Example 1 | sec-BuLi | −78 | 3.14 | 39 |
| Test Example 2 | sec-BuLi | −90 | 3.14 | 34 |
| Test Example 3 | n-BuLi | −78 | 3.14 | 61 |
| Test Example 4 | n-BuLi | −90 | 3.14 | 62 |
| Test Example 5 | sec-BuLi | −78 | 12.6 | 42 |
| Test Example 6 | sec-BuLi | −90 | 12.6 | 41 |

TABLE 1-continued

| | Organolithium compound | Temperature T (° C.) | Residence time t (sec) | Yield (%) |
|---|---|---|---|---|
| Test Example 7 | n-BuLi | −78 | 12.6 | 64 |
| Test Example 8 | n-BuLi | −90 | 12.6 | 58 |

In Table 1, Bu represents a butyl group.

From the results of Test Examples 1 to 8, it has been found that the fluorine-containing substituted compound can be produced by using a microreactor under the same temperature conditions as the conventional ones. With respect to the type of the organolithium compound, it has been found that the yield is higher when n-butyllithium is used than when sec-butyllithium is used.

Next, the following tests were performed for the purpose of examining the effects of the continuous methanol quenching and the solution introduction flow rate on the yield of the fluorine-containing substituted compound.

Test Example 9

Microreactor

Figure 3:
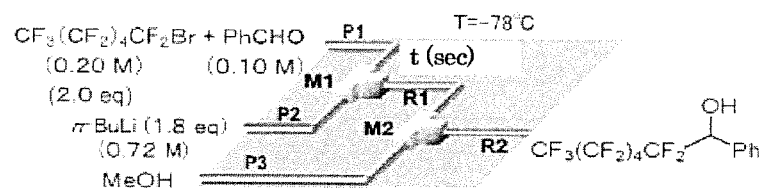
FIG. 3 is a diagram illustrating an outline of the reaction system in Test. Examples 9 to 14.

The microreactor used in present Test Example is, as shown in FIG. 3, constituted with T-shaped micromixers (M1, M2), micro tube reactors (R1, R2), and tube reactors (P1, P2, P3) for precooling.

For both of the micromixer M1 and the micromixer M2, T-shaped micromixers (micromixers 1 and 2, manufactured by Sankoh Seiki Kogyo Co., Ltd., inner diameter: 250 μm or 500 μm, see FIG. 3) were used. For the micro tube reactors and the tube reactors for precooling, a stainless steel tube (outer diameter: 1/16 inch (1.58 mm), inner diameter: 1,000 μm) manufactured by GL Sciences Inc. was used. The residence time was regulated, not by changing the flow rate, but by changing the length of the stainless steel tube. By submerging the whole of the microreactor in a thermostatic bath, the reaction temperature was set at −78° C.

<Preparation of Solutions to be Introduced into Microreactor>

The solutions to be introduced into the microreactor were prepared in the same manner as in Test Example 1 except that in Test Example 1, the concentrations of $CF_3(CF_2)_5Br$ and benzaldehyde were set at 0.20 M and 0.10 M, respectively, and a 0.72 M n-butyllithium solution was prepared by diluting n-butyllithium (manufactured by Kanto Chemical Co., Inc.) with hexane.

<Reaction Conditions>

Into the T-shaped mixer M1, the mixed solution of $CF_3(CF_2)_5Br$ and benzaldehyde and the n-butyllithium solution were liquid-transferred at the flow rates of 6.00 mL/min and 1.50 mL/min, respectively, by using syringe pumps. The solutions were mixed in the micromixer M1, and were allowed to undergo continuous reaction in the tube reactor. Methanol (manufactured by Wako Pure Chemical Industries, Ltd.) was introduced from one inlet of the microreactor M2. In the micromixer M2, by mixing the reactants and the methanol with each other, methanol quenching was performed (see FIG. 3).

The residence time in the tube reactor R1 (inner diameter: 1,000 μm, length: 12.5 cm) was set at 0.785 sec.

The mixed reaction solution was discarded for a few minutes until the reaction was stabilized and then taken into a sampling tube for 30 sec.

<Measurement of Yield>

The yield of the fluorine-containing substituted compound was measured in the same manner as in Test Example 1. The result thus obtained is shown in Table 2.

Test Examples 10 to 14

In each of Test Examples 10 to 14, the yield of the fluorine-containing substituted compound in the same manner as in Test Example 9 except that in Test Example 9, the flow rates (mL/min) of the introduction of the solutions and the residence time t (sec) in the tube reactor were altered to the combination shown in Table 2. The results thus obtained are shown in Table 2.

The residence time t was altered from 0.785 sec to 3.14 sec or 12.6 sec by changing the length of the tube reactor from 12.5 cm to 50 cm or 200 cm, respectively.

TABLE 2

| | Flow rate (mL/min) of $CF_3(CF_2)_5Br$:benzaldehyde mixed solution | Flow rate (mL/min) of n-BuLi | Residence time t (sec) | Yield (%) |
|---|---|---|---|---|
| Test Example 9 | 6.00 | 1.50 | 0.785 | 76 |
| Test Example 10 | 6.00 | 1.50 | 3.14 | 81 |
| Test Example 11 | 6.00 | 1.50 | 12.6 | 77 |
| Test Example 12 | 9.00 | 2.25 | 0.785 | 81 |
| Test Example 13 | 9.00 | 2.25 | 3.14 | 85 |
| Test Example 14 | 9.00 | 2.25 | 12.6 | 80 |

In Table 2, Bu represents a butyl group.

From the results of Test Examples 9 to 14, it has been found that the yield of the fluorine-containing substituted compound can be drastically improved by performing the methanol quenching by using a microreactor. It has also been found that by increasing the flow rates of the introduction of the organofluorine compound, the organolithium compound and the electrophile into the microreactor, the yield of the fluorine-containing substituted compound can be improved.

Example 1

Microreactor

Figure 4:
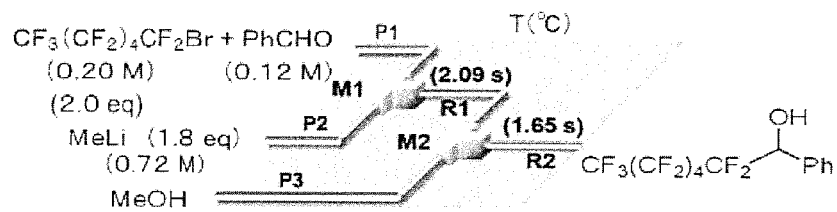
FIG. 4 is a diagram illustrating an outline of the reaction system in Examples 1 to 10 and Comparative Examples 1 to 5.

The microreactor used in present Example is constituted so as to include micromixers composed of a T-shaped tube fitting, and tube reactors connected downstream of the micromixers respectively (see FIG. 4).

—Micromixers—

As the micromixers (in FIG. 4, denoted by "M1" and "M2"), custom-made products manufactured by Sankoh Seiki Kogyo Co., Ltd. were used (it is possible to obtain equivalents by requesting the production on the basis of the description in present Example). The micromixers used in present Example each have inside thereof a first introduction path, a second introduction path and a portion of the flow path with which these introduction paths are merged, and the inner diameters of these introduction paths are the same as each other inside the micromixer. Accordingly, hereinafter, these inner diameters are collectively referred to as "the inner diameter of the micromixer."

—Tube Reactors—

As the tube reactors (in FIG. 4, denoted by "R1" and "R2"), stainless steel tubes manufactured by GL Sciences Inc. were used. As the liquid transfer pump, a syringe pump Model 11 Plus manufactured by Harvard Apparatus Inc. was used. The regulation of the reaction temperature was performed by submerging the whole of the microreactor in a thermostatic bath.

<Preparation of Solutions to be Introduced into Microreactor>

By diluting $CF_3(CF_2)_4CF_2Br$ (tridecafluorohexyl bromide, manufactured by Tokyo Chemical Industry Co., Ltd.), an organofluorine compound and benzaldehyde, an electrophile, with a mixed solution composed of THF and diethyl ether ($Et_2O$) (volume ratio: THF/$Et_2O$=2/1), a mixed solution of $CF_3(CF_2)_4CF_2Br$ and benzaldehyde having the concentrations of 0.10 M and 0.12 M, respectively, was prepared. By diluting methyllithium (MeLi, manufactured by Kanto Chemical Co., Inc.) with diethyl ether ($Et_2O$), a 0.42 M methyllithium solution was prepared.

<Reaction Conditions>

The prepared mixed solution of 0.10 M $CF_3(CF_2)_4CF_2Br$ and 0.12 M benzaldehyde was introduced from one inlet of the microreactor M1, and the prepared 0.42 M methyllithium solution was introduced from the other inlet of the microreactor. The solutions were each sucked into a gas-tight syringe, and then liquid-transferred into the microreactor by using a syringe pump manufactured by Harvard Apparatus Inc.

The solutions were mixed in the micromixer M1, and were allowed to undergo continuous reaction in the tube reactor. Methanol was introduced from one inlet of the microreactor M2. In the micromixer M2, by mixing the reactants with the methanol, the fluorine-containing substituted compound was produced (see FIG. 4).

As shown in FIG. 4, the microreactor is constituted with T-shaped micromixers (M1, M2), micro tube reactors (R1, R2), and tube reactors (P1, P2, P3) for precooling.

For both of the micromixer M1 and the micromixer M2, T-shaped micromixers (manufactured by Sankoh Seiki Kogyo Co., Ltd., inner diameter: 250 μm or 500 μm see FIG. 4) were used. For the micro tube reactors and the tube reactors for precooling, a stainless steel tube (outer diameter: 1/16 inch (1.58 mm), inner diameter: 1,000 μm) manufactured by GL Sciences Inc. was used. By submerging the whole of the microreactor in a thermostatic bath, the reaction temperature was set at 0° C.

Into the first T-shaped mixer M1 (inner diameter: 250 μm), the mixed solution of $CF_3(CF_2)_4CF_2Br$ and methyllithium and the methyllithium solution were liquid-transferred at the flow rates of 9.00 mL/min and 2.25 mL/min, respectively, by using syringe pumps.

Into the second T-shaped mixer M2 (inner diameter: 500 μm), methanol was liquid-transferred at the flow rate of 2.25 mL/min.

The residence time in the tube reactor R1 (inner diameter: 1,000 μm, length: 50 cm) was set at 2.09 sec, and the residence time in the tube reactor R2 (inner diameter: 1,000 μm, length: 50 cm) was set at 1.65 sec.

For each of the tube reactors (P1, P2, P3) for precooling, the inner diameter used was 1,000 μm and the length used was 100 cm.

The mixed reaction solution was discarded for a few minutes until the reaction was stabilized and then taken into a sampling tube for 30 sec.

<Measurement of Yield>

The yield of the fluorine-containing substituted compound was determined in the same manner as in Test Example 1. The result thus obtained is shown in Table 3.

Examples 2 to 10 and Comparative Examples 1 to 5

In each of Examples 2 to 10 and Comparative Examples 1 to 5, the fluorine-containing substituted compound was produced and the yield thereof was measured in the same manner as in Example 1 except that in Example 1, the type of the organolithium compound, the type of the solvent for the organofluorine compound and the electrophile and the reaction temperature T (° C.) were altered as shown in Table 1. The results thus obtained are shown in Table 1.

TABLE 3

| | Solvent | Temperature (° C.) | $CF_3(CF_2)_4CF_2X$ | Yield (%) |
|---|---|---|---|---|
| Ex. 1 | THF/$Et_2O$ | 0 | $CF_3(CF_2)_4CF_2Br$ | 75 |
| Ex. 2 | THF/$Et_2O$ | −48 | $CF_3(CF_2)_4CF_2Br$ | 93 |
| Comp. Ex. 1 | THF/$Et_2O$ | −78 | $CF_3(CF_2)_4CF_2Br$ | 94 |
| Ex. 3 | THF | 0 | $CF_3(CF_2)_4CF_2Br$ | 64 |
| Ex. 4 | THF | −48 | $CF_3(CF_2)_4CF_2Br$ | 95 |
| Comp. Ex. 2 | THF | −78 | $CF_3(CF_2)_4CF_2Br$ | 97 |
| Ex. 5 | $Et_2O$ | 0 | $CF_3(CF_2)_4CF_2Br$ | 85 |
| Ex. 6 | $Et_2O$ | −48 | $CF_3(CF_2)_4CF_2Br$ | 90 |
| Comp. Ex. 3 | $Et_2O$ | −78 | $CF_3(CF_2)_4CF_2Br$ | 83 |
| Ex. 7 | THF/$Et_2O$ | 0 | $CF_3(CF_2)_4CF_2I$ | 31 |
| Ex. 8 | THF/$Et_2O$ | −48 | $CF_3(CF_2)_4CF_2I$ | 18 |
| Comp. Ex. 4 | THF/$Et_2O$ | −78 | $CF_3(CF_2)_4CF_2I$ | 9 |
| Ex. 9 | $Et_2O$ | 0 | $CF_3(CF_2)_4CF_2I$ | 97 |
| Ex. 10 | $Et_2O$ | −48 | $CF_3(CF_2)_4CF_2I$ | 86 |
| Comp. Ex. 5 | $Et_2O$ | −78 | $CF_3(CF_2)_4CF_2I$ | 77 |

In Table 3, X represents an iodine atom or a bromine atom, and Et represents an ethyl group.

Example 11

Microreactor

Figure 5:
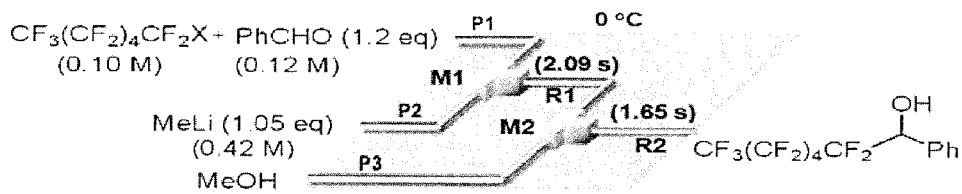
FIG. 5 is a diagram illustrating an outline of the reaction system in Examples 11 to 22.

The microreactor used in Example 11 is constituted so as to include micromixers composed of a T-shaped tube fitting, and tube reactors connected downstream of the micromixers respectively (see FIG. 5). The same micromixers and the same tube reactors as in Example 1 were used.

<Preparation of Solutions to be Introduced>

By diluting $CF_3CF_2I$ (iodopentafluoroethane, manufactured by Aldrich Corp.) and benzaldehyde with diethyl ether ($Et_2O$), a mixed solution of $CF_3CF_2I$ and benzaldehyde having the concentrations of 0.10 M and 0.12 M, respectively, was prepared. By diluting diethyl ether ($Et_2O$), a 0.12 M solution was prepared. By diluting methyllithium (MeLi) with diethyl ether ($Et_2O$), a 0.42 M methyllithium solution was prepared.

<Reaction Conditions>

The prepared mixed solution of $CF_3CF_2I$ and benzaldehyde was introduced from one inlet of the microreactor M1, and the prepared methyllithium solution was introduced from the other inlet of the microreactor. The solutions were each sucked into a gas-tight syringe, and then liquid-transferred into the microreactor by using a syringe pump manufactured by Harvard Apparatus Inc.

The solutions were mixed in the micromixer M1, and were allowed to undergo continuous reaction in the tube reactor, and methanol was introduced from one inlet of the microreactor M2. In the micromixer M2, the reactants and the methanol were mixed with each other, and methanol quenching was performed (see FIG. 5).

As shown in FIG. 5, the microreactor is constituted with T-shaped micromixers (M1, M2), micro tube reactors (R1, R2), and tube reactors (P1, P2, P3) for precooling.

For both of the micromixer M1 and the micromixer M2, T-shaped micromixers (micromixer 1, manufactured by Sankoh Seiki Kogyo Co., Ltd., inner diameter: 250 μm or 500 μm, see FIG. 2) were used. For the micro tube reactors and the tube reactors for precooling, a stainless steel tube (outer diameter: 1/16 inch (1.58 mm), inner diameter: 1,000 μm) manufactured by GL Sciences Inc. was used. By submerging the whole of the microreactor in a thermostatic bath, the reaction temperature was set at 0° C.

Into the first T-shaped mixer M1 (inner diameter: 250 μm), the mixed solution of $CF_3CF_2I$ (iodopentafluoroethane) and methyllithium and the methyllithium solution were liquid-transferred at the flow rates of 9.00 mL/min and 2.25 mL/min, respectively, by using syringe pumps.

Into the second T-shaped mixer M2 (inner diameter: 500 μm), methanol was liquid-transferred at the flow rate of 3.00 mL/min.

The residence time in the tube reactor R1 (inner diameter: 1,000 μm, length: 50 cm) was set at 2.09 sec, and the residence time in the tube reactor R2 (inner diameter: 1,000 μm, length: 50 cm) was set at 1.65 sec.

For each of the tube reactors (P1, P2, P3) for precooling, the inner diameter used was 1,000 μm and the length used was 100 cm.

The mixed reaction solution was discarded for a few minutes until the reaction was stabilized and then taken into a sampling tube for 30 sec.

<Measurement of Yield>

The yield of the fluorine-containing substituted compound was measured in the same manner as in Example 1. The result thus obtained is shown in Table 4.

Examples 12 to 22

In each of Examples 12 to 22, the fluorine-containing substituted compound was produced and the yield thereof was measured in the same manner as in Example 11 except that in Example 11, $CF_3CF_2I$ (iodopentafluoroethane) as the organofluorine compound and benzaldehyde as the electrophile were altered to the components shown in Table 1. The results thus obtained are shown in Table 4.

TABLE 4

| | $CF_3(CF_2)_nCF_2X$ | Electrophile | Fluorine-containing substituted compound | Yield (%) |
|---|---|---|---|---|
| Ex. 11 | $CF_3CF_2I$ |  | 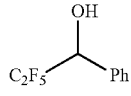 | 84 |
| Ex. 12 | $CF_3CF_2CF_2I$ |  | 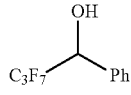 | 80 |
| Ex. 13 | $CF_3(CF_2)_2CF_2I$ |  | 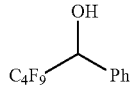 | 85 |
| Ex. 14 | $CF_3(CF_2)_3CF_2I$ |  | 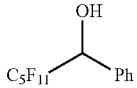 | 86 |
| Ex. 15 | $CF_3(CF_2)_4CF_2I$ |  | 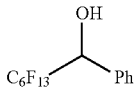 | 80 |
| Ex. 16 | $CF_3(CF_2)_4CF_2Br$ |  | 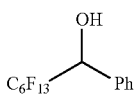 | 71 |
| Ex. 17 | $CF_3(CF_2)_4CF_2I$ |  | 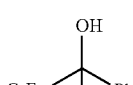 | 70 |
| Ex. 18 | $CF_3(CF_2)_4CF_2I$ | 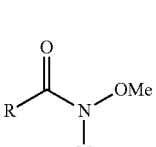 (R = $C_4H_8$—Ph) | 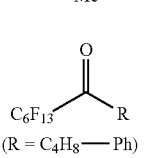 (R = $C_4H_8$—Ph) | 42 |

TABLE 4-continued

| | $CF_3(CF_2)_nCF_2X$ | Electrophile | Fluorine-containing substituted compound | Yield (%) |
|---|---|---|---|---|
| Ex. 19 | $CF_3(CF_2)_4CF_2I$ |  | 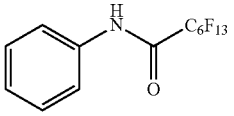 | 79 |
| Ex. 20 | $CF_3(CF_2)_4CF_2I$ | 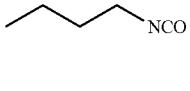 | 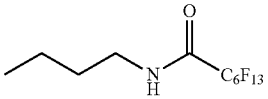 | 86 |
| Ex. 21 | $CF_3(CF_2)_4CF_2I$ | $Me_3SiOTf$ | $C_6F_{13}SiMe_3$ | 30 |
| Ex. 22 | $CF_3(CF_2)_4CF_2I$ | $Bu_3SnCl$ | $C_6F_{13}SnBu_3$ | 2 |

In Table 4, X represents an iodine atom or a bromine atom, Me represents a methyl group, Bu represents an n-butyl group, Ph represents a phenyl group, and Tf represents a trifluoromethylsulfonyl group.

From the results of Examples 11 to 22, it has been found that the use of a microreactor enables the production of the fluorine-containing substituted compound without using an excessive amount of perfluoroalkyl halide, at an industrially practicable temperature, without performing complicated operations. In Examples 14, 15, 18, 19, 20 and 21, novel fluorine-containing substituted compounds were able to be produced.

Example 23

In present Example, the following operations were performed for the purpose of elucidating the relation between the reaction temperature T (° C.) and the residence time t (sec) in the microreactor in the case of the use of an electrophile resulting in a low yield of the target fluorine-containing compound.

<Preparation of Solution>

$CF_3(CF_2)_4CF_2I$ (tridecafluorohexyl iodide, manufactured by Tokyo Chemical Industry Co., Ltd.) as the organofluorine compound and methyllithium were introduced into a microreactor and allowed to react with each other, and then the reaction product and $Bu_3SnCl$ (tributyltin chloride, manufactured by Aldrich Corp.) were allowed to react with each other to form a perfluoro group-substituted compound.

Figure 6:
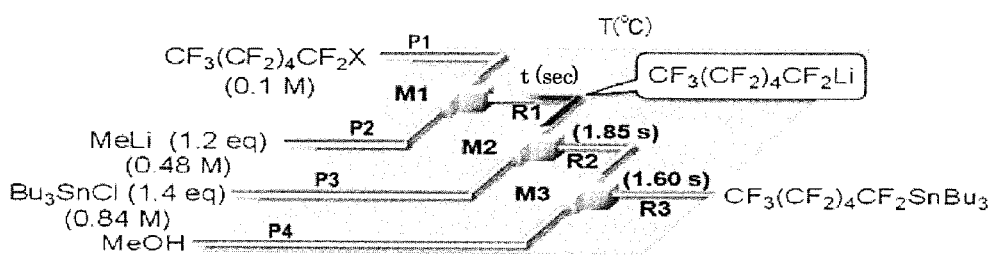
FIG. 6 is a diagram illustrating an outline of the reaction system in Example 23.

Next, methanol was introduced as the reaction terminator into the microreactor, the continuous methanol quenching with the fluorine-substituted compound was performed, to produce $CF_3(CF_2)_4CF_2SnBu_3$ (perfluorohexyl tributyltin) (see FIG. 6).

<Microreactor>

The microreactor is constituted with T-shaped micromixers (M1, M2, M3), micro tube reactors (R1, R2, M3), and the tube reactors (P1, P2, P3, P4) for precooling (see, FIG. 6).

For each of the micromixer M1, micromixer M2 and micromixer M3, a T-shaped micromixer (manufactured by Sankoh Seiki Kogyo Co., Ltd., inner diameter of M1: 250 μm, inner diameters of M2 and M3: 500 μm, see FIG. 6) was used.

For the micro tube reactors and the tube reactors for precooling, a stainless steel tube (outer diameter: 1/16 inch (1.58 mm), inner diameter: 1,000 μm) manufactured by GL Sciences Inc. was used.

<Reaction Conditions>

The residence time was regulated, not by changing the flow rate, but by changing the length of the tube reactor to 3.5 cm, 6.0 cm, 12.5 cm, 25 cm, 50 cm, 100 cm and 200 cm. By submerging the microreactor in a prescribed thermostatic bath (the temperature T of the thermostatic bath: −48° C., −58° C., −68° C. and −78° C.), the reaction temperature was set.

$CF_3(CF_2)_4CF_2I$, an organofluorine compound, was diluted with diethyl ether to prepare a 0.14 M solution of $CF_3(CF_2)_4CF_2I$. Methyllithium, an organolithium compound, was diluted with diethyl ether to prepare a 0.48 M solution of methyllithium. $Bu_3SnCl$, an electrophile, was diluted with diethyl ether to prepare a 0.84 M solution of $Bu_3SnCl$. The solutions were each sucked into a gas-tight syringe, and then liquid-transferred into the microreactor by using a syringe pump manufactured by Harvard Apparatus Inc.

Into the first T-shaped mixer M1 (inner diameter: 250 μm), the solution of $CF_3(CF_2)_4CF_2I$ and the solution of methyllithium were liquid-transferred at the flow rates of 9.00 mL/min and 2.25 mL/min, respectively, by using syringe pumps.

Into the second T-shaped mixer M2 (inner diameter: 500 μm), the solution of $Bu_3SnCl$ was liquid-transferred at the flow rate of 1.50 mL/min.

Into the third T-shaped mixer M3 (inner diameter: 250 μm), a methanol solution was liquid-transferred at the flow rate of 2.00 mL/min.

The residence time t in the tube reactor R1 (inner diameter: 1,000 μm) was varied as described above, and set at 0.15 sec, 0.25 sec, 0.52 sec, 1.1 sec, 2.1 sec, 4.2 sec and 8.4 sec. The residence time in the tube reactor R2 (inner diameter: 1,000 μm, length: 50 cm) was set at 1.85 sec, and the residence time in the tube reactor R3 (inner diameter: 1,000 μm, length: 50 cm) was set at 1.60 sec.

For each of the tube reactors (P1, P2, P3, P4) for precooling, the inner diameter used was 1,000 μm and the length used was 100 cm.

<Measurement of Yield>

The finally obtained solution was treated in the same manner as in Example 1, and the yield of the tridecafluorohexyl-tin fluorine-containing substituted compound was determined in the same manner as in Example 1. The results thus obtained are shown in FIG. 7.

Figure 7:
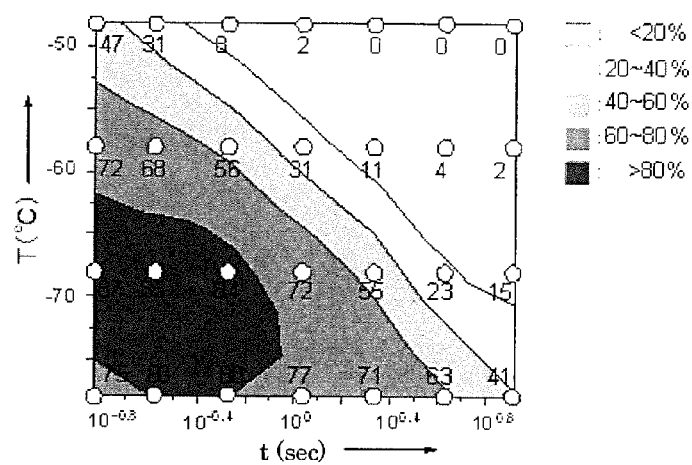
FIG. 7 is a graph showing the yield of the fluorine-containing substituted compound against the reaction temperature T (° C.) and the residence time t (sec) in Example 23.

In FIG. 7, the yield of the tridecafluorohexyl-tin is shown on the counter plot with the X-axis representing the residence time and the Y-axis representing the reaction temperature.

From the results of Example 23, it has been found that as the relation between the reaction temperature T (° C.) and the residence time t (sec), from the viewpoint of the yield of the fluorine-containing substituted compound, it is preferable to satisfy the following relation, T≤−3.8t−48.

Example 24

Figure 8:
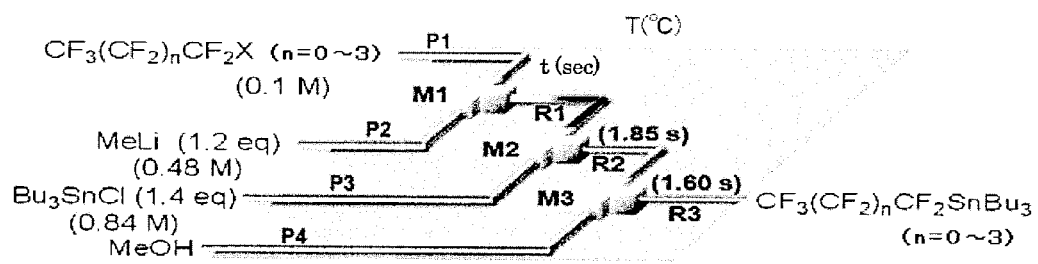
FIG. 8 is a diagram illustrating an outline of the reaction system in Examples 24 to 27.
Figure 9:
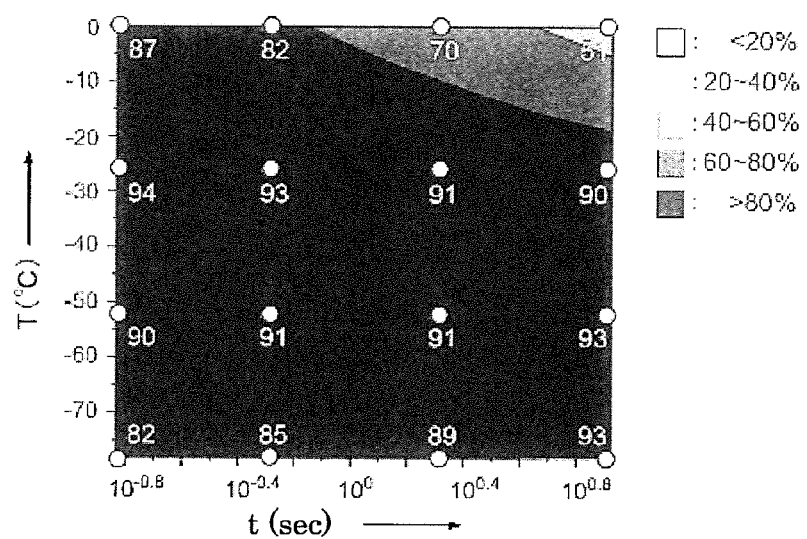
FIG. 9 is a graph showing the yield of the fluorine-containing substituted compound against the reaction temperature T (° C.) and the residence time t (sec) in Example 24.

The yield of the fluorine-containing substituted compound was determined in the same manner as in Example 23 except that in Example 23, the organofluorine compound was altered from $CF_3(CF_2)_4CF_2I$ (tridecafluorohexyl iodide) to $CF_3CF_2I$ (iodopentafluoroethane, manufactured by Aldrich Corp.), and the temperature T of the thermostatic bath was altered to 0° C., −26° C., −52° C. and −78° C. (see FIG. 8). The results thus obtained are shown in FIG. 9.

From the results of Example 24, it has been found that from the viewpoint of the yield of the fluorine-containing substituted compound, it is preferable to satisfy the relation T≤0, and it is more preferable to satisfy the relation T≤−26.

Example 25

Figure 10:
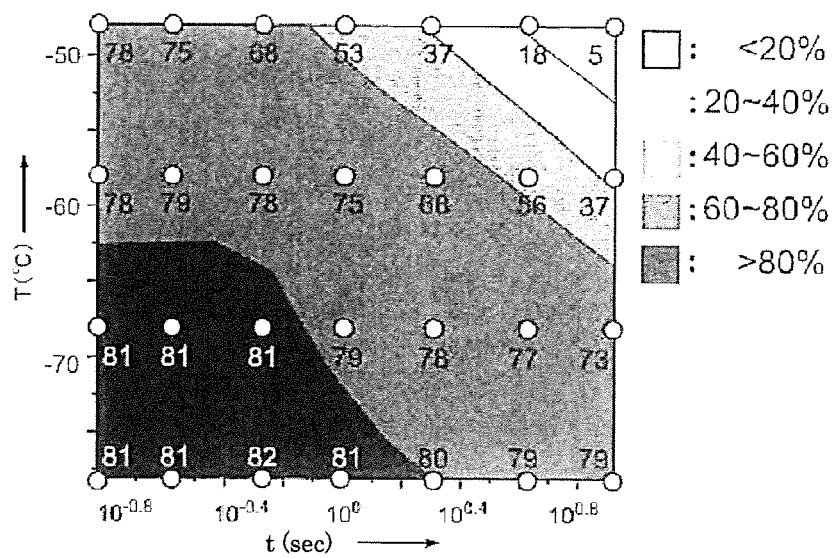
FIG. 10 is a graph showing the yield of the fluorine-containing substituted compound against the reaction temperature T (° C.) and the residence time t (sec) in Example 25.

The yield of the fluorine-containing substituted compound was determined in the same manner as in Example 23 except that in Example 23, the organofluorine compound was altered from $CF_3(CF_2)_4CF_2I$ (tridecafluorohexyl iodide) to $CF_3CF_2CF_2I$ (heptafluoropropyl iodide, manufactured by Tokyo Chemical Industry Co., Ltd.) (see FIG. 8). The results thus obtained are shown in FIG. 10.

From the results of Example 25, it has been found that from the viewpoint of the yield of the fluorine-containing substituted compound, it is preferable to satisfy the relation T≤−3.2t−45.

Example 26

Figure 11:
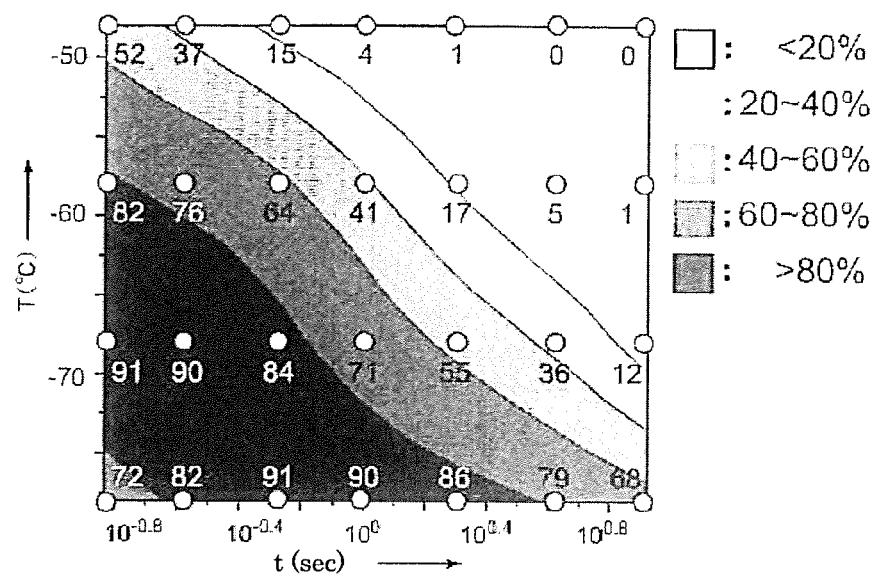
FIG. 11 is a graph showing the yield of the fluorine-containing substituted compound against the reaction temperature T (° C.) and the residence time t (sec) in Example 26.

The yield of the fluorine-containing substituted compound was determined in the same manner as in Example 23 except that in Example 23, the organofluorine compound was altered from $CF_3(CF_2)_2CF_2I$ (nonafluorobutyl iodide, manufactured by Tokyo Chemical Industry Co., Ltd.) (see FIG. 8). The results thus obtained are shown in FIG. 11.

From the results of Example 26, it has been found that from the viewpoint of the yield of the fluorine-containing substituted compound, it is preferable to satisfy the relation T≤−5.1t−47.

Example 27

Figure 12:
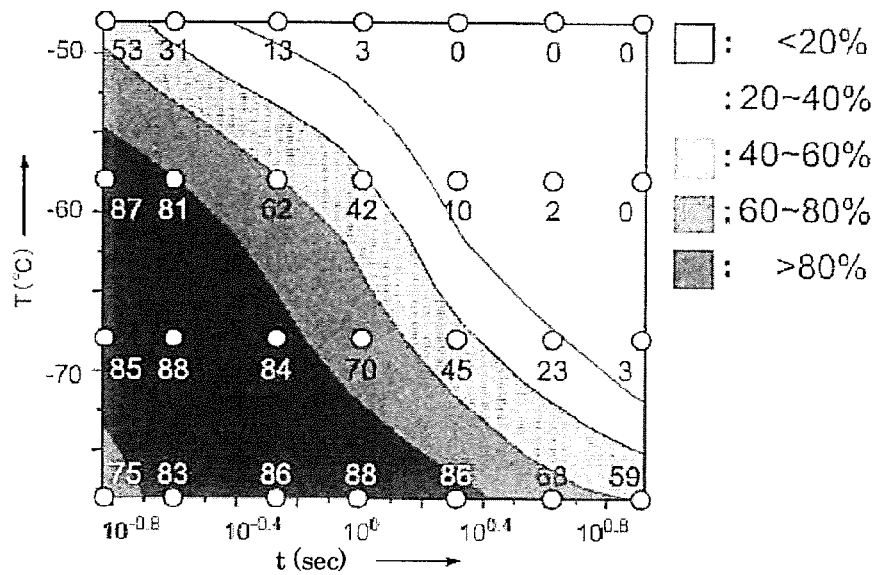
FIG. 12 is a graph showing the yield of the fluorine-containing substituted compound against the reaction temperature T (° C.) and the residence time t (sec) in Example 27.

The yield of the fluorine-containing substituted compound was determined in the same manner as in Example 23 except that in Example 23, the organofluorine compound was altered from $CF_3(CF_2)_4CF_2I$ (tridecafluorohexyl iodide) to $CF_3(CF_2)_3CF_2I$ (undecafluoropentyl iodide, manufactured by Tokyo Chemical Industry Co., Ltd.) (see FIG. 8). The results thus obtained are shown in FIG. 12.

From the results of Example 27, it has been found that from the viewpoint of the yield of the fluorine-containing substituted compound, it is preferable to satisfy the relation T≤−7.1t−47.

From foregoing Examples 23 to 27, the stability of $CF_3(CF_2)_nCF_2Li$ is high for n=0 (the number of carbon atoms is 2), $CF_3(CF_2)_nCF_2Li$ becomes unstable for n=1 or more (the number of carbon atoms is 3 or more); however, it is considered that for n=2 or more, $CF_3(CF_2)_nCF_2Li$ has almost the same stability irrespective of the length of the alkyl chain.

Examples 28 to 32

In each of Examples 28 to 32, the fluorine-containing substituted compound was produced and the yield thereof was measured in the same manner as in Example 23 except that in Example 23, the temperature of the thermostatic bath (the reaction temperature) T was set at −68° C., the residence time was set at 0.15 sec, and the organofluorine compound and the electrophile were altered to the combination shown in Table 5 presented below. The results thus obtained are shown in Table 5. Table 5 also shows the yields in Examples 23 to 27, in the cases where the temperature of the thermostatic bath (reaction temperature) T=−68° C. and the residence time t=0.15 sec.

TABLE 5

| | $CF_3(CF_2)_nCF_2X$ | Electrophile | Produced fluorine-containing compound | Yield (%) |
|---|---|---|---|---|
| Ex. 24 | $CF_3CF_2I$ | $Bu_3SnCl$ | $C_2F_5SnBu_3$ | 98 |
| Ex. 25 | $CF_3CF_2CF_2I$ | $Bu_3SnCl$ | $C_3F_7SnBu_3$ | 81 |
| Ex. 26 | $CF_3(CF_2)_2CF_2I$ | $Bu_3SnCl$ | $C_4F_9SnBu_3$ | 91 |
| Ex. 27 | $CF_3(CF_2)_3CF_2I$ | $Bu_3SnCl$ | $C_5F_{11}SnBu_3$ | 85 |
| Ex. 23 | $CF_3(CF_2)_4CF_2I$ | $Bu_3SnCl$ | $C_6F_{13}SnBu_3$ | 87 |
| Ex. 28 | $CF_3(CF_2)_4CF_2Br$ | $Bu_3SnCl$ | $C_6F_{13}SnBu_3$ | 75 |
| Ex. 29 | $CF_3(CF_2)_4CF_2I$ | $Me_3SiOTf$ | $C_6F_{13}SiMe_3$ | 82 |
| Ex. 30 | $CF_3(CF_2)_4CF_2I$ | Ph-NCO | Ph-NH-C(O)-$C_6F_{13}$ | 87 |
| Ex. 31 | $CF_3(CF_2)_4CF_2I$ | Bu-NCO | Bu-NH-C(O)-$C_6F_{13}$ | 91 |
| Ex. 32 | $CF_3(CF_2)_4CF_2I$ | $Ph_2PCl$ | $C_6F_{13}PPh_2$ | 48 |

In Table 5, X represents an iodine atom or a bromine atom, Me represents a methyl group, and Bu represents an n-butyl group, and Ph represents a phenyl group.

From Table 5, it has been found that the use of the microreactor allows the use of those types of electrophiles which, in conventional batch-type reactors, result in an extremely low yield of the target fluorine-containing substituted compound or preclude obtaining the target fluorine-containing substituted compound, and enables drastic improvement of the yield of the target fluorine-containing substituted compound. In Examples 27, 29, 30 and 31, novel fluorine-containing substituted compounds were able to be produced.

Example 33

Figure 13:
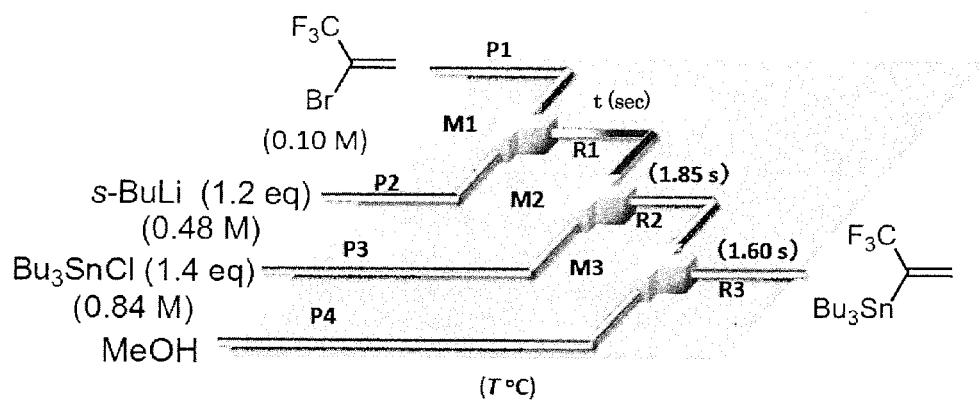
FIG. 13 is a diagram illustrating an outline of the reaction system in Example 33.

The yield of the fluorine-containing substituted compound was determined in the same manner as in Example 23 except that in Example 23, the organofluorine compound was altered from $CF_3(CF_2)_4CF_2I$ (tridecafluorohexyl iodide) to 1-(trifluoromethyl)vinyl bromide (manufactured by Tokyo Chemical Industry Co., Ltd.), the temperature T of the thermostatic bath was set at −28° C., −48° C., −65° C., −78° C. and −90° C., and the residence time t in the tube reactor R1 was set at 0.014 sec, 0.055 sec, 0.22 sec, 0.79 sec, 3.1 sec, 6.3 sec and 13 sec (see FIG. 13). The results thus obtained are shown in FIG. 14.

Figure 14:
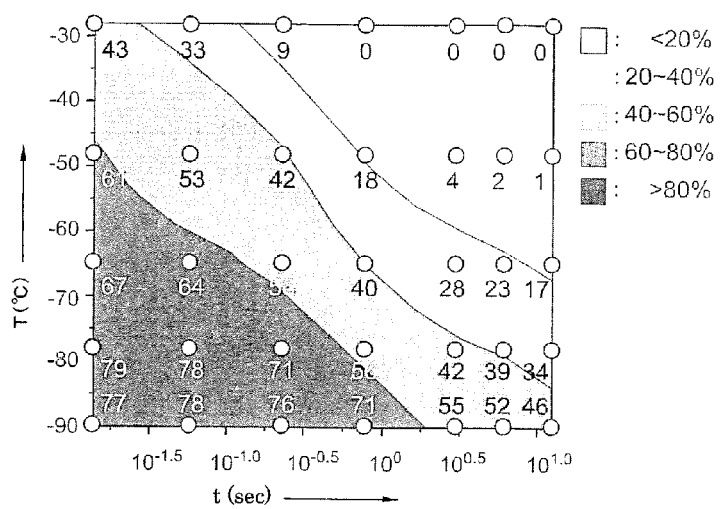
FIG. 14 is a graph showing the yield of the fluorine-containing substituted compound against the reaction temperature T (° C.) and the residence time t (sec) in Example 33.

From FIG. 14, it has been found that in the temperature region higher than the conventional reaction temperature (−105° C.; see Nadano R, Fuchibe K, Ikeda M, Takahashi H, Ichikawa J. Chem Asian J. 2010; 5(8):1875-1883), 1-(trifluoromethyl)vinyllithium can be produced and the target fluorine-containing substituted compound can be obtained in a shorter time. It has also been found that from the viewpoint of the yield of the fluorine-containing substituted compound, it is preferable to satisfy the relation $T \leq -7.2t-45$.

Examples 34 and 35

In each of Examples 34 and 35, the fluorine-containing substituted compound was produced and the yield thereof was measured in the same manner as in Example 33 except that in Example 33, the temperature of the thermostatic bath (reaction temperature) T was set at −78° C., the residence time was set at 0.055 sec, and the electrophile was altered to the compound shown in Table 6 presented below. The results thus obtained are shown in Table 6. Table 6 also shows the yield in the case in Example 33 where the temperature of the thermostatic bath (reaction temperature) T=−78° C. and the residence time t=0.055 sec.

TABLE 6

| | Organofluorine compound | Electrophile | Produced fluorine-containing compound | Yield (%) |
|---|---|---|---|---|
| Ex. 33 | CF₃-C(=CH₂)-Br | Bu₃SnCl | CF₃-C(=CH₂)-SnBu₃ | 79 |
| Ex. 34 | CF₃-C(=CH₂)-Br | PhCHO | CF₃-C(=CH₂)-CH(OH)Ph | 76 |
| Ex. 35 | CF₃-C(=CH₂)-Br | Ph-CO-CH₃ | CF₃-C(=CH₂)-C(CH₃)(OH)Ph | 27 |

In Table 6, Bu represents a normal-butyl group and Ph represents a phenyl group.

From Table 6, it has been found that the use of the microreactor allows the production of the target fluorine-containing substituted compound at an industrially practicable temperature, without using complicated apparatuses and without performing complicated operations. In Example 34 and 35, novel fluorine-containing substituted compounds were able to be produced.

INDUSTRIAL APPLICABILITY

According to the method for producing a fluorine-containing substituted compound of the present invention, the fluorine-containing substituted compound can be produced at an industrially practicable temperature, without using complicated apparatuses and without performing complicated operations; the yield of the fluorine-containing substituted compound, which is low on the basis of conventional production methods, can be improved; further, novel fluorine-containing substituted compounds, which cannot be produced by conventional production methods, can be produced; consequently the method for producing a fluorine-containing substituted compound of the present invention can be preferably used in various fields of, for example, medicines, agricultural chemicals, liquid crystals and fuel cells.

What is claimed is:
1. A method for producing a fluorine-containing substituted compound, the method comprising: introducing a fluoroalkylhalide and an organolithium compound into a first flow path in a microreactor provided with a plurality of flow paths capable of mixing a plurality of liquids, to thereby obtain a reaction product; and introducing, into a second flow path in the microreactor, the reaction product and an electrophile exhibiting electrophilic effect on the reaction product, to thereby obtain a fluorine-containing substituted compound.

2. The method according to claim 1, wherein the fluoroalkylhalide is a fluoroalkyl halide having 6 carbon atoms, and wherein a temperature T (° C.) inside the first flow path of the microreactor into which the fluoroalkylhalide and the organolithium compound have been introduced and a residence time t (sec) thereof in the first flow path of the microreactor satisfy the following relation: $T \leq -3.8t-48$.

3. The method according to claim 1, wherein the fluoroalkylhalide is a fluoroalkyl halide having 2 carbon atoms, and wherein a temperature T (° C.) inside the first flow path of the microreactor into which the fluoroalkylhalide and the organolithium compound have been introduced and a residence time t (sec) thereof in the first flow path of the microreactor satisfy the relations $-100 \leq T \leq 0$ and $0.15 \leq t \leq 8.4$, respectively.

4. The method according to claim 1, wherein the fluoroalkylhalide is a fluoroalkyl halide having 3 carbon atoms, and wherein a temperature T (° C.) inside the first flow path of the microreactor into which the fluoroalkylhalide and the organolithium compound have been introduced and a residence time t (sec) thereof in the first flow path of the microreactor satisfy the following relation: $T \leq -3.2t-45$.

5. The method according to claim 1, wherein the fluoroalkylhalide is a fluoroalkyl halide having 4 carbon atoms, and wherein a temperature T (° C.) inside the first flow path of the microreactor into which the fluoroalkylhalide and the organolithium compound have been introduced and a residence time t (sec) thereof in the first flow path of the microreactor satisfy the following relation: $T \leq -5.1t-47$.

6. The method according to claim 1, wherein the fluoroalkylhalide is a fluoroalkyl halide having 5 carbon atoms, and wherein a temperature T (° C.) inside the first flow path of the microreactor into which the fluoroalkylhalide and the organolithium compound have been introduced and a residence time t (sec) thereof in the first flow path of the microreactor satisfy the following relation: $T \leq -7.1t-47$.

7. The method according to claim 1, further comprising continuously introducing, into a third flow of the microreactor, the fluorine-containing substituted compound and methanol.

8. The method according to claim 1, wherein the fluoroalkylhalide, the organolithium compound and the electrophile are dissolved in diethyl ether and introduced into the second path of the microreactor.

9. The method according to claim 1, wherein the fluoroalkylhalide is a perfluoroalkyl halide.

10. The method according to claim 1, wherein the organolithium compound is butyllithium.

11. The method according to claim 1, wherein the electrophile is an aldehyde, a ketone or an isocyanate, or any combination thereof.

12. A method for producing a fluorine-containing substituted compound, the method comprising: introducing, into a microreactor provided with a flow path capable of mixing a plurality of liquids, an organofluorine compound, an organolithium compound, and an electrophile exhibiting electrophilic effect on a reaction product between the organofluorine compound and the organolithium compound, under conditions of temperature being −55° C. or higher.

13. The method according to claim 12, wherein the temperature is −20° C. or higher.

14. The method according to claim 12, wherein the temperature is 0° C. or higher.

15. The method according to claim 12, further comprising continuously introducing, into the microreactor, the fluorine-containing substituted compound and methanol.

16. The method according to claim 12, wherein the organofluorine compound, the organolithium compound and the electrophile are dissolved in diethyl ether and introduced into the microreactor.

17. The method according to claim 12, wherein the organofluorine compound is a perfluoroalkyl halide.

18. The method according to claim 12, wherein the organolithium compound is butyllithium.

19. The method according to claim 12, wherein the electrophile is an aldehyde, a ketone or an isocyanate, or any combination thereof.

* * * * *